US012410484B2

(12) United States Patent
Canady et al.

(10) Patent No.: US 12,410,484 B2
(45) Date of Patent: Sep. 9, 2025

(54) METHOD FOR COLD PLASMA INDUCED CELL DEATH IN BREAST CANCER CELLS BY 8-oxoG MODIFICATION AND DEGRADATION OF HISTONE mRNA

(71) Applicant: Jerome Canady Research Institute for Advanced Biological and Technological Sciences, Takoma Park, MD (US)

(72) Inventors: Jerome Canady, Takoma Park, MD (US); Saravana Murthy, Takoma Park, MD (US); Xiaoqian Cheng, Takoma Park, MD (US); Taisen Zhuang, Takoma Park, MD (US)

(73) Assignee: Jerome Canady Research Institute for Advanced Biological and Technological Sciences, Takoma Park, MD (US)

( * ) Notice: Subject to any disclaimer, the term of this patent is extended or adjusted under 35 U.S.C. 154(b) by 0 days.

(21) Appl. No.: 18/576,506

(22) PCT Filed: Jul. 5, 2022

(86) PCT No.: PCT/US2022/036133
§ 371 (c)(1),
(2) Date: Jan. 4, 2024

(87) PCT Pub. No.: WO2023/283194
PCT Pub. Date: Jan. 12, 2023

(65) Prior Publication Data
US 2024/0263244 A1    Aug. 8, 2024

Related U.S. Application Data

(60) Provisional application No. 63/218,449, filed on Jul. 5, 2021.

(51) Int. Cl.
*C12Q 1/6886* (2018.01)
(52) U.S. Cl.
CPC ..... *C12Q 1/6886* (2013.01); *C12Q 2600/158* (2013.01)
(58) Field of Classification Search
None
See application file for complete search history.

(56) References Cited

U.S. PATENT DOCUMENTS

2007/0060743 A1  3/2007 Tang et al.
2010/0120627 A1  5/2010 Belouchi et al.
2021/0187021 A1  6/2021 Canady et al.

OTHER PUBLICATIONS

Kang et al. Detection of 8-oxoguanine and apurinic/apyrimidinic sites using a fluorophore-labeled probe with cell-penetrating ability. BMC Molecular and Cell Biology 20:54 (12 pages). (Year: 2019).*
Ye, X. et al. Defective Sphase chromatin assembly causes DNA damage, activation of the S phase checkpoint, and S phase arrest. Mol Cell 11, 341-351 (2003).
Meeks-Wagner, D. & Hartwell, L. H. Normal stoichiometry of histone dimer sets is necessary for high fidelity of mitotic chromosome transmission. Cell 44, 43-52 (1986).
Kurat, C. F. et al. Restriction of histone gene transcription to S phase by phosphorylation of a chromatin boundary protein. Genes Dev 25, 2489-2501 (2011).
Park, S. et al. Cold Atmospheric Plasma Restores Paclitaxel Sensitivity to Paclitaxel-Resistant Breast Cancer Cells by Reversing Expression of Resistance-Related Genes. Cancers (Basel) 11 (2019).
Xiang, L., Xu, X., Zhang, S., Cai, D. & Dai, X. Cold atmospheric plasma conveys selectivity on triple negative breast cancer cells both in vitro and in vivo. Free Radic Biol Med 124, 205-213 (2018).
Liu, Y. et al. Selective effects of non-thermal atmospheric plasma on triple-negative breast normal and carcinoma cells through different cell signaling pathways. Sci Rep 7, 7980 (2017).
Lee, S. et al. Cold atmospheric plasma restores tamoxifen sensitivity in resistant MCF-7 breast cancer cell. Free Radic Biol Med 110, 280-290, doi:10.1016/j.freeradbiomed.2017.06.017 (2017).
Zhu, W. et al. Synergistic Effect of Cold Atmospheric Plasma and Drug Loaded Core-shell Nanoparticles on Inhibiting Breast Cancer Cell Growth. Sci Rep 6, 21974 (2016).
Wang, M. et al. Cold atmospheric plasma for selectively ablating metastatic breast cancer cells. PLoS One 8, e73741 (2013).
Kim, S. J., Chung, T. H., Bae, S. H. & Leem, S. H. Induction of apoptosis in human breast cancer cells by a pulsed atmospheric pressure plasma jet. Applied Physics Letters 97 (2010).
Gonzalez-Rivera et al. "RNA oxidation in chromatin modification and DNA-damage response following exposure to formaldehyde," Sci Rep, Oct. 6, 2020 (Oct. 6, 2020), vol. 10, 16545, pp. 1-16. entire document.
Cheng el al. "Canady Helios Cold Plasma Induces Breast Cancer Cell Death by Oxidation of Histone mRNA," Int J Mol Sci, Sep. 3, 2021 (Sep. 3, 2021), vol. 22, 9578, pp. 1-22. entire document.
Russnes, H. G., Lingjaerde, O. C., Borresen-Dale, A. L. & Caldas, C. Breast Cancer Molecular Stratification: From Intrinsic Subtypes to Integrative Clusters. Am J Pathol 187, 2152-2162 (2017).
Hammond, M. E. et al. American Society of Clinical Oncology/College of American Pathologists guideline recommendations for immunohistochemical testing of estrogen and progesterone receptors in breast cancer. J Clin Oncol 28, 2784-2795 (2010).

(Continued)

*Primary Examiner* — Samuel C Woolwine
(74) *Attorney, Agent, or Firm* — 24IP Law Group USA, PLLC; Timothy R. DeWitt

(57) ABSTRACT

A method for inducing cell death in breast cancer regardless of subtyping through histone mRNA oxidation and degradation during the early S-phase of the cell cycle. A method for monitoring levels of oxidized histone mRNA in breast cancer cells, comprising the steps of isolating histone mRNA from breast cancer cells, incubating the histone mRNA with a peptide according to SEQ ID NO: 1 and determining the levels of oxidized histone mRNA by measuring the fluorescence intensity.

8 Claims, 29 Drawing Sheets

Specification includes a Sequence Listing.

(56) References Cited

OTHER PUBLICATIONS

Holliday, D. L. & Speirs, V. Choosing the right cell line for breast cancer research. Breast Cancer Research 13 (2011).
Dai, X., Cheng, H., Bai, Z. & Li, J. Breast Cancer Cell Line Classification and Its Relevance with Breast Tumor Subtyping. J Cancer 8, 3131-3141 (2017).
Howlader, N. et al. US incidence of breast cancer subtypes defined by joint hormone receptor and HER2 status. J Natl Cancer Inst 106 (2014).
Adams, S. et al. Current Landscape of Immunotherapy in Breast Cancer: A Review. JAMA Oncol (2019).
Yan, D., Sherman, J. H. & Keidar, M. Cold atmospheric plasma, a novel promising anti-cancer treatment modality. Oncotarget 8, 15977-15995 (2017).
Fridman, G. et al. Floating Electrode Dielectric Barrier Discharge Plasma in Air Promoting Apoptotic Behavior in Melanoma Skin Cancer Cell Lines. Plasma Chemistry and Plasma Processing 27, 163-176 (2007).
Schneider, C. et al. Cold atmospheric plasma causes a calcium influx in melanoma cells triggering CAP-induced senescence. Sci Rep 8, 10048 (2018).
Cheng, X. et al. The effect of tuning cold plasma composition on glioblastoma cell viability. PLoS One 9, e98652 (2014).
Privat-Maldonado, A., Gorbanev, Y., Dewilde, S., Smits, E. & Bogaerts, A. Reduction of Human Glioblastoma Spheroids Using Cold Atmospheric Plasma: The Combined Effect of Short- and Long-Lived Reactive Species. Cancers (Basel) 10 (2018).
Xu, D. et al. Effect of cold atmospheric plasma treatment on the metabolites of human leukemia cells. Cancer Cell Int 19, 135 (2019).
Rowe, W. et al. The Canady Helios Cold Plasma Scalpel Significantly Decreases Viability in Malignant Solid Tumor Cells in a Dose-Dependent Manner. Plasma 1, 177-188 (2018).
Yan, D. et al. Cold plasma-based control of the activation of pancreatic adenocarcinoma cells. Journal of Physics D: Applied Physics 52 (2019).
Ma, J. et al. Targeting Nrf2-mediated heme oxygenase-1 enhances non-thermal plasma-induced cell death in non-small-cell lung cancer A549 cells. Arch Biochem Biophys 658, 54-65 (2018).
Duan, J., Lu, X. & He, G. The selective effect of plasma activated medium in an in vitro co-culture of liver cancer and normal cells. Journal of Applied Physics 121 (2017).
Park, S. B. et al. Differential Epigenetic Effects of Atmospheric Cold Plasma on MCF-7 and MDA-MB-231 Breast Cancer Cells. PLoS One 10, e0129931 (2015).
Xu, X. et al. Quantitative assessment of cold atmospheric plasma anti-cancer efficacy in triple-negative breast cancers. Plasma Processes and Polymers 15 (2018).
Weiss, M. et al. Cold Atmospheric Plasma Treatment Induces Anti-Proliferative Effects in Prostate Cancer Cells by Redox and Apoptotic Signaling Pathways. PLoS One 10, e0130350 (2015).
Ishaq, M., Han, Z. J., Kumar, S., Evans, M. D. M. & Ostrikov, K. K. Atmospheric-Pressure Plasma- and TRAIL-Induced Apoptosis in TRAIL-Resistant Colorectal Cancer Cells. Plasma Processes and Polymers 12, 574-582 (2015).
Chernets, N., Kurpad, D. S., Alexeev, V., Rodrigues, D. B. & Freeman, T. A. Reaction Chemistry Generated by Nanosecond Pulsed Dielectric Barrier Discharge Treatment is Responsible for the Tumor Eradication in the B16 Melanoma Mouse Model. Plasma Process Polym 12, 1400-1409 (2015).
Chen, Z. et al. A Novel Micro Cold Atmospheric Plasma Device for Glioblastoma Both In Vitro and In Vivo. Cancers (Basel) 9 (2017).
Utsumi, F. et al. Effect of indirect nonequilibrium atmospheric pressure plasma on anti-proliferative activity against chronic chemo-resistant ovarian cancer cells in vitro and in vivo. PLoS One 8, e81576 (2013).
Xu, D. et al. Systemic study on the safety of immuno-deficient nude mice treated by atmospheric plasma-activated water. Plasma Science and Technology 20 (2018).
Liu, J.-R. et al. Low-temperature plasma induce melanoma apoptosis by triggering a p53/PIGs/caspase-dependent pathway in vivo and in vitro. Journal of Physics D: Applied Physics 52 (2019).
Mizuno, K., Yonetamari, K., Shirakawa, Y., Akiyama, T. & Ono, R. Anti-tumor immune response induced by nanosecond pulsed streamer discharge in mice. Journal of Physics D: Applied Physics 50, 12LT01 (2017).
Mizuno, K. et al. Plasma-Induced Suppression of Recurrent and Reinoculated Melanoma Tumors in Mice. IEEE Transactions on Radiation and Plasma Medical Sciences 2, 353-359 (2018).
Chen, G. et al. Transdermal cold atmospheric plasma-mediated immune checkpoint blockade therapy. Proc Natl Acad Sci U S A 117, 3687-3692 (2020).
Freund, E. et al. Physical plasma-treated saline promotes an immunogenic phenotype in CT26 colon cancer cells in vitro and in vivo. Sci Rep 9, 634 (2019).
Rowe, W. et al. The Canady Helios Cold Plasma Scalpel Significantly Decreases Viability in Malignant Solid Tumor Cells in a Dose-Dependent Manner. Plasma 1, 177-188 published 2018.
Cheng, X. et al. Treatment of Triple-Negative Breast Cancer Cells with the Canady Cold Plasma Conversion System: Preliminary Results. Plasma 1, 218-228 (2018).
Ly, L. et al. Canady cold plasma conversion system treatment: An effective inhibitor of cell viability in breast cancer molecular subtypes. Clinical Plasma Medicine (2020).
Dai, X., Bazaka, K., Thompson, E. W. & Ostrikov, K. K. Cold Atmospheric Plasma: A Promising Controller of Cancer Cell States. Cancers (Basel) 12 (2020).
Ishaq, M., Evans, M. D. & Ostrikov, K. K. Atmospheric pressure gas plasma-induced colorectal cancer cell death is mediated by Nox2-ASK1 apoptosis pathways and oxidative stress is mitigated by Srx-Nrf2 anti-oxidant system. Biochim Biophys Acta 1843, 2827-2837 (2014).
Xia, J. et al. Cold atmospheric plasma induces apoptosis of melanoma cells via Sestrin2-mediated nitric oxide synthase signaling. J Biophotonics 12, e201800046 (2019).
Rodriguez-Campos, A. & Azorin, F. RNA is an integral component of chromatin that contributes to its structural organization. PLoS One 2, e1182 (2007).
Wu, S. K., Roberts, J. T., Balas, M. M. & Johnson, A. M. RNA matchmaking in chromatin regulation. Biochem Soc Trans 48, 2467-2481 (2020).
Kornberg, R. D. & Lorch, Y. Twenty-five years of the nucleosome, fundamental particle of the eukaryote chromosome. Cell 98, 285-294 (1999).
Khorasanizadeh, S. The nucleosome: from genomic organization to genomic regulation. Cell 116, 259-272 (2004).
Heintz, N. The regulation of histone gene expression during the cell cycle. Biochem Biophys Acta 1088, 327-339 (1991).
Marzluff, W. F. & Duronio, R. J. Histone mRNA expression: multiple levels of cell cycle regulation and important developmental consequences. Curr Opin Cell Biol 14, 692-699 (2002).
Osley, M. A. The regulation of histone synthesis in the cell cycle. Annu Rev Biochem 60, 827-861 (1991).
Stein, G. S., Stein, J. L., Van Wijnen, A. J. & Lian, J. B. Transcriptional control of cell cycle progression: the histone gene is a paradigm for the G1/S phase and proliferation/differentiation transitions. Cell Biol Int 20, 41-49 (1996).
Gunjan, A., Paik, J. & Verreault, A. Regulation of histone synthesis and nucleosome assembly. Biochimie 87, 625-635 (2005).
Deran, M., Pulvino, M., Greene, E., Su, C. & Zhao, J. Transcriptional activation of histone genes requires NPAT-dependent recruitment of TRRAP-Tip60 complex to histone promoters during the G1/S phase transition. Mol Cell Biol 28, 435-447 (2008).
Miele, A. et al. HiNF-P directly links the cyclin E/CDK2/p220NPAT pathway to histone H4 gene regulation at the G1/S phase cell cycle transition. Mol Cell Biol 25, 6140-6153 (2005).
Fletcher, C., Heintz, N. & Roeder, R. G. Purification and characterization of OTF-1, a transcription factor regulating cell cycle expression of a human histone H2b gene. Cell 51, 773-781 (1987).
Mei, Q. et al. Regulation of DNA replication-coupled histone gene expression. Oncotarget 8, 95005-95022 (2017).

(56) References Cited

OTHER PUBLICATIONS

Zhao, J. Coordination of DNA synthesis and histone gene expression during normal cell cycle progression and after DNA damage. Cell Cycle 3, 695-697 (2004).

* cited by examiner

FIG. 16B

| Histone Genes | HIST1-H2AB | HIST1-H2AC | HIST1-H2AI | HIST1-H2BJ | HIST1-H2BK | HIST1-H2BN | HIST1-H2BO | HIST1-H3A | HIST1-H3B | HIST1-H3C | HIST1-H3H | HIST1-H4B | HIST2-H3D | HIST4-H4 |
|---|---|---|---|---|---|---|---|---|---|---|---|---|---|---|
| t Test with Bonferroni Correction | | | | | | | | | | | | | | |
| CAP-ZERO-HRS-IP Vs MOCK-ZERO-HRS-IP | * | * | * | * | * | * |  | * | * | * | * | * | * | * |
| CAP-ONE-HRS-IP Vs MOCK-ONE-HRS-IP | * | * | * | * | * | * |  | * | * | * | * | * | * | * |
| CAP-ZERO-HRS-IP Vs MOCK-ZERO-HRS-IN | * | * | * | * | * | * |  | * | * | * | * | * | * | * |
| CAP-ONE-HRS-IP Vs MOCK-ONE-HRS-IN |  |  |  |  | * | * | * |  |  |  |  |  |  |  |
| CAP-ZERO-HRS-IP Vs CAP-ONE-HRS-IP |  |  |  |  |  |  |  |  |  |  |  |  |  |  |

FIG. 18B

METHOD FOR COLD PLASMA INDUCED CELL DEATH IN BREAST CANCER CELLS BY 8-oxoG MODIFICATION AND DEGRADATION OF HISTONE mRNA

CROSS-REFERENCE TO RELATED APPLICATIONS

The present application is a U.S. national stage of International Application Ser. No. PCT/US2022/036133 filed on Jul. 5, 2022, which claims the benefit of the filing date of U.S. Provisional Patent Application Ser. No. 63/218,449 filed by the present inventors on Jul. 5, 2021. The aforementioned applications are hereby incorporated by reference in their entirety.

SEQUENCE LISTING

The instant application contains a Sequence Listing which has been submitted electronically in XML format and is hereby incorporated by reference in its entirety. Said XML copy, created on Apr. 22, 2025, is named 9101_160US_SL.xml and is 5,068 bytes in size.

BACKGROUND OF THE INVENTION

Field of the Invention

The present invention relates to a method for inducing cell death of breast cancer cells regardless of subtyping through histone mRNA oxidation and degradation during an early S-phase of a cell cycle.

Brief Description of the Related Art

Breast carcinomas can be categorized into different entities based on clinical behavior, histologic features, and/or by biological properties, which is important for the discovery of novel treatment, the study of tumor evolution, and the identification of mechanisms of treatment resistance (Russnes, H. G., Lingjaerde, O. C., Borresen-Dale, A. L. & Caldas, C. Breast Cancer Molecular Stratification: From Intrinsic Subtypes to Integrative Clusters. Am J Pathol 187, 2152-2162 (2017)). Tumors with expression of either estrogen receptor (ER) or progesterone receptor (PR) in at least 1% of tumor cells are categorized as hormone receptor-positive ($HR^+$) (Hammond, M. E. et al. American Society of Clinical Oncology/College Of American Pathologists guideline recommendations for immunohistochemical testing of estrogen and progesterone receptors in breast cancer. J Clin Oncol 28, 2784-2795 (2010)) and intrinsic subtypes of breast cancers are classified into luminal A ($ER^+PR^{+/-}HER2^-$), luminal B ($ER^+PR^{+/-}HER2^+$), basal-like ($ER^-PR^-HER2^-$), and HER2-positive ($ER^-PR^-HER2^+$) (Holliday, D. L. & Speirs, V. Choosing the right cell line for breast cancer research. Breast Cancer Research 13 (2011) and Dai, X., Cheng, H., Bai, Z. & Li, J. Breast Cancer Cell Line Classification and Its Relevance with Breast Tumor Subtyping. J Cancer 8, 3131-3141 (2017)).

The systemic and local treatment are addressed by 3 major breast cancer subtypes: $HR^+HER2^-$, $HER2^+$, and TNBC (Dai, X., Cheng, H., Bai, Z. & Li, J. Breast Cancer Cell Line Classification and Its Relevance with Breast Tumor Subtyping. J Cancer 8, 3131-3141, (2017)) of which 70% of the cases are $HR^+HER2^-$, and use of endocrine agents to downregulate ER signaling. $HER2^+$ breast cancer constitutes 15-20% of the cases, and HER2 targeted therapy including anti-HER2 antibodies such as trastuzumab and pertuzumab, and small-molecule tyrosine kinase inhibitors such as lapatinib and neratinib. Basal-like (TNBC) makes up approximately 15% of breast cancer cases and their molecular pathophysiology remains poorly understood. Howlader, N. et al. US incidence of breast cancer subtypes defined by joint hormone receptor and HER2 status. J Natl Cancer Inst 106 (2014). In March 2019 the Food and Drug Administration (FDA) granted the first immunotherapy, an accelerated approval for the immunotherapy drug atezolizumab in combination with chemotherapy for the initial treatment with locally advanced or metastatic TNBC with positive programed cell death 1 ligand (PD-L1) expression (Adams, S. et al. Current Landscape of Immunotherapy in Breast Cancer: A Review. JAMA Oncol (2019)).

Cold atmospheric plasma (CAP) as a novel anti-cancer therapy across various cancer types has been investigated for more than a decade and its significant anti-cancer capability over 20 cancer types in vitro (Yan, D., Sherman, J. H. & Keidar, M. Cold atmospheric plasma, a novel promising anti-cancer treatment modality. Oncotarget 8, 15977-15995 (2017)) including breast cancer (Fridman, G. et al. Floating Electrode Dielectric Barrier Discharge Plasma in Air Promoting Apoptotic Behavior in Melanoma Skin Cancer Cell Lines. Plasma Chemistry and Plasma Processing 27, 163-176 (2007), Schneider, C. et al. Cold atmospheric plasma causes a calcium influx in melanoma cells triggering CAP-induced senescence. Sci Rep 8, 10048 (2018), Cheng, X. et al. The effect of tuning cold plasma composition on glioblastoma cell viability. PLoS One 9, e98652 (2014), Privat-Maldonado, A., Gorbanev, Y., Dewilde, S., Smits, E. & Bogaerts, A. Reduction of Human Glioblastoma Spheroids Using Cold Atmospheric Plasma: The Combined Effect of Short- and Long-Lived Reactive Species. Cancers (Basel) 10 (2018), Xu, D. et al. Effect of cold atmospheric plasma treatment on the metabolites of human leukemia cells. Cancer Cell Int 19, 135 (2019), Rowe, W. et al. The Canady Helios Cold Plasma Scalpel Significantly Decreases Viability in Malignant Solid Tumor Cells in a Dose-Dependent Manner. Plasma 1, 177-188 (2018), Yan, D. et al. Cold plasma-based control of the activation of pancreatic adenocarcinoma cells. Journal of Physics D: Applied Physics 52 (2019), Ma, J. et al. Targeting Nrf2-mediated heme oxygenase-1 enhances non-thermal plasma-induced cell death in non-small-cell lung cancer A549 cells. Arch Biochem Biophys 658, 54-65 (2018), Duan, J., Lu, X. & He, G. The selective effect of plasma activated medium in an in vitro co-culture of liver cancer and normal cells. Journal of Applied Physics 121 (2017), Park, S. B. et al. Differential Epigenetic Effects of Atmospheric Cold Plasma on MCF-7 and MDA-MB-231 Breast Cancer Cells. PLoS One 10, e0129931 (2015), Xu, X. et al. Quantitative assessment of cold atmospheric plasma anti-cancer efficacy in triple-negative breast cancers. Plasma Processes and Polymers 15 (2018), Weiss, M. et al. Cold Atmospheric Plasma Treatment Induces Anti-Proliferative Effects in Prostate Cancer Cells by Redox and Apoptotic Signaling Pathways. PLoS One 10, e0130350 (2015), Ishaq, M., Han, Z. J., Kumar, S., Evans, M. D. M. & Ostrikov, K. K. Atmospheric-Pressure Plasma- and TRAIL-Induced Apoptosis in TRAIL-Resistant Colorectal Cancer Cells. Plasma Processes and Polymers 12, 574-582 (2015)) demonstrated. In vivo studies of CAP with mouse models on the subcutaneous or intracranial tumor nodules with a CAP device (Chernets, N., Kurpad, D. S., Alexeev, V., Rodrigues, D. B. & Freeman, T. A. Reaction Chemistry Generated by Nanosecond Pulsed Dielectric Barrier Discharge Treatment is Responsible for the Tumor Eradication in the B16 Melanoma Mouse Model. Plasma Process Polym 12, 1400-1409 (2015) and Chen, Z. et al. A Novel Micro Cold Atmospheric Plasma Device for Glioblastoma Both In Vitro and In Vivo. Cancers (Basel) 9 (2017)), or indirect-treatment with CAP-activated medium/ water (Utsumi, F. et al. Effect of indirect nonequilibrium atmospheric pressure plasma on anti-proliferative activity against chronic chemo-resistant ovarian cancer cells in vitro and in vivo. PLoS One 8, e81576 (2013), Xu, D. et al. Systemic study on the safety of immuno-deficient nude mice treated by atmospheric plasma-activated water. Plasma Science and Technology 20 (2018), and Liu, J.-R. et al. Low-temperature plasma induced melanoma apoptosis by triggering a p53/PIGs/caspase-dependent pathway in vivo and in vitro. Journal of Physics D: Applied Physics 52 (2019)) have effectively reduced tumor growth rate and induce cancer cell death, in addition to immune-system activation (Mizuno, K., Yonetamari, K., Shirakawa, Y., Akiyama, T. & Ono, R. Anti-tumor immune response induced by nanosecond pulsed streamer discharge in mice. *Journal of Physics D: Applied Physics* 50, 12LT01 (2017), Mizuno, K. et al. Plasma-Induced Suppression of Recurrent and Reinoculated Melanoma Tumors in Mice. IEEE Transactions on Radiation and Plasma Medical Sciences 2, 353-359 (2018), Chen, G. et al. Transdermal cold atmospheric plasma-mediated immune checkpoint blockade therapy. Proc Natl Acad Sci USA 117, 3687-3692 (2020) and Freund, E. et al. Physical plasma-treated saline promotes an immunogenic phenotype in CT26 colon cancer cells in vitro and in vivo. Sci Rep 9, 634 (2019)). The first clinical trial using CAP for the treatment of cancer in the United States approved by Food Drug Administration (FDA) was received by Jerome Canady Research Institute for Advanced Biological and Technological Sciences (JCRI-ABTS) and US Medical Innovations, LLC (USMI). Canady Helios Cold Plasma™ developed at JCRI-ABTS integrated cold plasma and a high frequency plasma electrosurgical system and demonstrated that the system and method effectively eliminate various types of solid tumors including breast carcinoma (Rowe, W. et al. The Canady Helios Cold Plasma Scalpel Significantly Decreases Viability in Malignant Solid Tumor Cells in a Dose-Dependent Manner. *Plasma* 1, 177-188, Cheng, X. et al. Treatment of Triple-Negative Breast Cancer Cells with the Canady Cold Plasma Conversion System: Preliminary Results. Plasma 1, 218-228 (2018) and Ly, L. et al. Canady cold plasma conversion system treatment: An effective inhibitor of cell viability in breast cancer molecular subtypes. Clinical Plasma Medicine (2020).

CAP induces cancer cell death and there has been evidence that the reactive oxygen species (ROS) and reactive nitrogen species (RNS) composing the cold plasma cocktail play an important role, as well as the species generated in the liquid phase when they are in contact with cell culture medium or bodily fluid. Dai, X., Bazaka, K., Thompson, E. W. & Ostrikov, K. K. Cold Atmospheric Plasma: A Promising Controller of Cancer Cell States. Cancers (Basel) 12 (2020). These species could induce apoptosis, cell cycle arrest and DNA damage in cells and tissues. The most baffling question is how CAP can selectively induce cell death in cancer cells, while keeping normal tissue intact. Previous studies have highlighted a few non-compendious evidence such as induction of oxidative stress through Srx-Nrf2 antioxidant system in colorectal cancer cells (Ishaq, M., Evans, M. D. & Ostrikov, K. K. Atmospheric pressure gas plasma-induced colorectal cancer cell death is mediated by Nox2-ASK1 apoptosis pathways and oxidative stress is mitigated by Srx-Nrf2 anti-oxidant system. Biochim Biophys Acta 1843, 2827-2837 (2014)), sestrin2-mediated nitric oxide synthase signaling (Xia, J. et al. Cold atmospheric plasma induces apoptosis of melanoma cells via Sestrin2-mediated nitric oxide synthase signaling. J Biophotonics 12, e201800046 (2019)) or CAP-induced epigenetic alterations (Park, S. B. et al. Differential Epigenetic Effects of Atmospheric Cold Plasma on MCF-7 and MDA-MB-231 Breast Cancer Cells. PLoS One 10, e0129931 (2015)), however, no study has emphasized the role of RNA in CAP-induced cell death. Several works have suggested that RNA may play an important role in the cellular response to oxidative stress. Moreover, RNA functions both as a structurally integral part (Rodriguez-Campos, A. & Azorin, F. RNA is an integral component of chromatin that contributes to its structural organization. PLoS One 2, e1182 (2007)) and as a regulator of chromatin (Wu, S. K., Roberts, J. T., Balas, M. M. & Johnson, A. M. RNA matchmaking in chromatin regulation. Biochem Soc Trans 48, 2467-2481 (2020)). The association of negatively charged DNA to the positively charged histones proteins are collectively called chromatin and the histone proteins play crucial roles in all cellular processes that involve chromosomal DNA, such as DNA replication, transcription, DNA repair, recombination, and chromosome segregation (Kornberg, R. D. & Lorch, Y. Twenty-five years of the nucleosome, fundamental particle of the eukaryote chromosome. Cell 98, 285-294 (1999) and Khorasanizadeh, S. The nucleosome: from genomic organization to genomic regulation. Cell 116, 259-272 (2004)). Their assembly into chromosomes and their biosynthesis are tightly regulated with DNA synthesis during the S phase of the cell cycle and their regulation occur at both the transcriptional and the posttranscriptional levels leading to several fold increase during S phase (Heintz, N. The regulation of histone gene expression during the cell cycle. Biochem Biophys Acta 1088, 327-339 (1991), Marzluff, W. F. & Duronio, R. J. Histone mRNA expression: multiple levels of cell cycle regulation and important developmental consequences. Curr Opin Cell Biol 14, 692-699 (2002), Osley, M. A. The regulation of histone synthesis in the cell cycle. Annu Rev Biochem 60, 827-861 (1991), Stein, G. S., Stein, J. L., Van Wijnen, A. J. & Lian, J. B. Transcriptional control of cell cycle progression: the histone gene is a paradigm for the G1/S phase and proliferation/differentiation transitions. Cell Biol Int 20, 41-49 (1996) and Gunjan, A., Paik, J. & Verreault, A. Regulation of histone synthesis and nucleosome assembly. Biochimie 87, 625-635 (2005)) when regulatory proteins directly bind to the subtype-specific regulatory elements (SSREs) in the promoters region of the histone genes such as (H1, H2A, H2B, H3, and H4) (Heintz, N. The regulation of histone gene expression during the cell cycle. Biochim Biophys Acta 1088, 327-339 (1991), Osley, M. A. The regulation of histone synthesis in the cell cycle. Annu Rev Biochem 60, 827-861 (1991), DeRan, M., Pulvino, M., Greene, E., Su, C. & Zhao, J. Transcriptional activation of histone genes requires NPAT-dependent recruitment of TRRAP-Tip60 complex to histone promoters during the G1/S phase transition. Mol Cell Biol 28, 435-447 (2008), Miele, A. et al. HiNF-P directly links the cyclin E/CDK2/p220NPAT pathway to histone H4 gene regulation at the G1/S phase cell cycle transition. Mol Cell Biol 25, 6140-6153 (2005) and Fletcher, C., Heintz, N. & Roeder, R. G. Purification and characterization of OTF-1, a transcription factor regulating cell cycle expression of a human histone H2b gene. Cell 51, 773-781 (1987)). Core histone overexpression outside of S phase is toxic, and deregulation of histone genes leads to loss of chromosomes resulting in DNA damage and cell death (Mei, Q. et al. Regulation of DNA replication-coupled histone gene expression. Oncotarget 8, 95005-95022 (2017), Zhao, J. Coordination of DNA synthesis and histone gene expression during normal cell cycle progression and after DNA damage. Cell Cycle 3, 695-697 (2004), Ye, X. et al. Defective S phase chromatin assembly causes DNA damage, activation of the S phase checkpoint, and S phase arrest. Mol Cell 11, 341-351 (2003), Meeks-Wagner, D. & Hartwell, L. H. Normal stoichiometry of histone dimer sets is necessary for high fidelity of mitotic chromosome transmission. Cell 44, 43-52 (1986) and Kurat, C. F. et al. Restriction of histone gene transcription to S phase by phosphorylation of a chromatin boundary protein. Genes Dev 25, 2489-2501 (2011)). Accumulation of mutations in genes that control cell proliferation eventually leads to cancerous state. These characteristics differentiate cancer from the normal cells and seemingly the S phase events occur more frequently in tumor than normal cells. 8 CAP effect on breast cancer cell lines have been studied repeatedly (Park, S. B. et al.

Differential Epigenetic Effects of Atmospheric Cold Plasma on MCF-7 and MDA-MB-231 Breast Cancer Cells. PLoS One 10, e0129931 (2015), Xu, X. et al. Quantitative assessment of cold atmospheric plasma anti-cancer efficacy in triple-negative breast cancers. Plasma Processes and Polymers 15 (2018), Park, S. et al. Cold Atmospheric Plasma Restores Paclitaxel Sensitivity to Paclitaxel-Resistant Breast Cancer Cells by Reversing Expression of Resistance-Related Genes. Cancers (Basel) 11 (2019), Xiang, L., Xu, X., Zhang, S., Cai, D. & Dai, X. Cold atmospheric plasma conveys selectivity on triple negative breast cancer cells both in vitro and in vivo. Free Radic Biol Med 124, 205-213 (2018), Liu, Y. et al. Selective effects of nonthermal atmospheric plasma on triple-negative breast normal and carcinoma cells through different cell signaling pathways. Sci Rep 7, 7980 (2017), Lee, S. et al. Cold atmospheric plasma restores tamoxifen sensitivity in resistant MCF-7 breast cancer cell. Free Radic Biol Med 110, 280-290, doi:10.1016/j.freeradbiomed.2017.06.017 (2017), Zhu, W. et al. Synergistic Effect of Cold Atmospheric Plasma and Drug Loaded Core-shell Nanoparticles on Inhibiting Breast Cancer Cell Growth. Sci Rep 6, 21974 (2016), Wang, M. et al. Cold atmospheric plasma for selectively ablating metastatic breast cancer cells. PLoS One 8, e73741 (2013) and Kim, S. J., Chung, T. H., Bae, S. H. & Leem, S. H. Induction of apoptosis in human breast cancer cells by a pulsed atmospheric pressure plasma jet. Applied Physics Letters 97 (2010)), suggesting CAP as a promising therapy for breast cancer. However, the differential effects of CAP on breast cancer of different molecular subtypes have yet been reported except for our previous study (Ly, L. et al. Canady cold plasma conversion system treatment: An effective inhibitor of cell viability in breast cancer molecular subtypes. Clinical Plasma Medicine (2020)). To understand CAP effect on breast cancer cell lines with different marker status, four breast cancer cell lines were tested with cold plasma at various dosages. The four cell lines chosen, MCF-7 (luminal A, ER$^+$PR$^+$HER2$^-$), BT-474 (luminal B, ER$^+$PR$^+$HER2$^+$), MDA-MB-231 (basal-like, ER$^-$PR$^-$HER2$^-$), and SK-BR-3 (ER$^-$PR$^-$HER2$^+$) were extensively studied in the literature and are representative cell lines for each subtype (Holliday, D. L. & Speirs, V. Choosing the right cell line for breast cancer research. Breast Cancer Research 13 (2011)). The aim of this study is to prove cold plasma as a precise therapy and reveal the anti-cancer mechanism of CAP for all breast cancer subtypes. In this study we are the first to report that degradation of histone RNA in breast cancer cell lines by cold plasma treatment leads to cell death, which is the key differentiating factor for the selective induction of apoptosis in breast cancer cells.

SUMMARY OF INVENTION

Breast cancer is the most common cancer among women worldwide. Its molecular receptor markers status and their mutational subtypes complicates clinical therapies. Cold atmospheric plasma (CAP) has shown promising results as an adjuvant therapy to selectively combat many cancers including breast cancer cells but not normal tissue. However, the underlying mechanism previously remained unexplored. To investigate the mechanism, four breast cancer cell lines with different marker status were tested using cold plasma at various power settings and treatment times. Cell biological and biochemical methods were used to monitor the differential progress of apoptosis on these cell lines. Cold plasma induced cell death in a dosage-dependent manner with each subtype requiring slightly different power or time settings to achieve 100% elimination. Inhibition of cell proliferation, induction of apoptosis, and arrest of cell cycle were observed when cells were monitored by Ki67 expression using confocal microscopy imaging and IncuCyte live cell imaging system for up to 72 hours post cold plasma treatment. Cell cycle analysis demonstrated that the cell death occurred at the end of G1 cycle without transitioning completely into S phase. RNASeq profiling and qRT-PCR analysis showed that at least 16 histone mRNA types were degraded after cold plasma treatment. Furthermore, in situ fluorescent probe and immunoprecipitation analysis confirmed that histone gene transcripts were degraded by 8-oxoguanine (8-oxoG) modification within 1 hour after cold plasma treatment. The expression of DNA damage responder genes by qRT-PCR was up-regulated 12 hours post cold plasma treatment indicating that 8-oxoG modification and degradation of histone mRNA rather than DNA damage is the primary cause of cell death induced by cold plasma treatment. Our report demonstrates for the first time that cold plasma effectively induced cell death in breast cancer regardless of subtyping through the histone mRNA oxidation and degradation during the early S-phase of the cell cycle as potential novel, a mechanism of CAP induced cell death.

In a preferred embodiment, the present invention is a method for monitoring levels of oxidized histone mRNA in breast cancer cells. The method comprises isolating histone mRNA from breast cancer cells, incubating the histone mRNA with a peptide according to SEQ.ID.1, and determining the levels of oxidized histone mRNA by measuring the fluorescence intensity. The fluorescence intensity may be determined by microscopy. The histone mRNA may be 8-oxoguanine modified. The breast cancer cells are treated with cold plasma prior to isolating the histone mRNA, The cold plasma treatment employs cold plasma at less than 35° C. The method may be performed 6, 24 or 48 hours post cold plasma treatment. The method further may comprise the step of a differential expression analysis for the isolated histone mRNAs wherein the isolated histone mRNA levels of histones selected from the group comprising HIST1H1C; HIST1H2AB; HIST1H2AC; HIST1H2AG; HIST1H2AI; HIST1H2BJ; HIST1H2BK; HIST1H2BN; HIST1H2BO; HIST1H3A; HIST1H3B; HIST1H3C; HIST1H3H; HIST1H4B; HIST2H3D and HIST4H4 are determined.

In another embodiment, the present invention is a peptide (Alexa 488-TaT-S3) synthesized by solid-phase peptide synthesis with the following sequence (Alexa 488) GVLRFIMESGAKGSEVVVSGGGYGRKKRRQRRR (SEQ.ID.1).

In yet another embodiment, the present invention is a method for cold plasma-induced cell death in breast cancer cells by 8-oxog modification and degradation of histone mrna.

BRIEF DESCRIPTION OF THE DRAWINGS

For a more complete understanding of the present invention and the advantages thereof, reference is now made to the following description and the accompanying drawings, in which:

FIG. 1A shows viability assay was performed 48 hours post treatment. Data was normalized to control group (no treatment) of each cell line respectively. FIGS. 1B-1E show confluence of MCF-7, BT-474, MDA-MB-231, and SK-BR-3 cells with or without CAP treatment over 72 hours. Student t test was performed on each treatment dosage and every hour post CAP treatment compared to NT (*p<0.05). NT=No Treatment; TNBC=Triple-negative breast cancer.

FIG. 7A shows averaged quantification plot of 'live', 'early apoptosis', and 'late apoptosis/dead' population of MCF-7 cells 24 h post CAP treatment. FIG. 7B shows averaged quantification plot of 'live', 'early apoptosis', and 'late apoptosis/dead' population of MCF-7 cells 48 h post CAP treatment (* above the bars denotes statistical significance of CAP treated group compared to corresponding No Treatment group. *p<0.05, p<0.01, and *p<0.001).

FIG. 8A shows averaged quantification plot of 'live', 'early apoptosis', and 'late apoptosis/dead' population of BT-474 cells 24 h post CAP treatment. FIG. 8B shows averaged quantification plot of 'live', 'early apoptosis', and 'late apoptosis/dead' population of BT-474 cells 48 h post CAP treatment (* above the bars denotes statistical significance of CAP treated group compared to corresponding No Treatment group. *p<0.05, p<0.01, and *p<0.001).

FIG. 9A is an averaged quantification plot of 'live', 'early apoptosis', and 'late apoptosis/dead' population of MDA-MB-231 cells 24 h post CAP treatment. FIG. 9B shows the averaged quantification plot of 'live', 'early apoptosis', and 'late apoptosis/dead' population of MDA-MB-231 cells 48 h post CAP treatment (* above the bars denotes statistical significance of CAP treated group compared to corresponding No Treatment group; * between FIGS. 9A and 9B denote statistical significance of the two groups. *p<0.05, p<0.01, and *p<0.001).

FIG. 10A shows averaged quantification plot of 'live', 'early apoptosis', and 'late apoptosis/dead' population of SK-BR-3 cells 24 h post CAP treatment. FIG. 10B shows averaged quantification plot of 'live', 'early apoptosis', and 'late apoptosis/dead' population of SK-BR-3 cells 48 h post CAP treatment (* above the bars denotes statistical significance of CAP treated group compared to corresponding No Treatment group; * between FIGS. 10A and 10B denote statistical significance of the two groups. *p<0.05, p<0.01, and *p<0.001).

DETAILED DESCRIPTION OF THE INVENTION

Figure 1A:
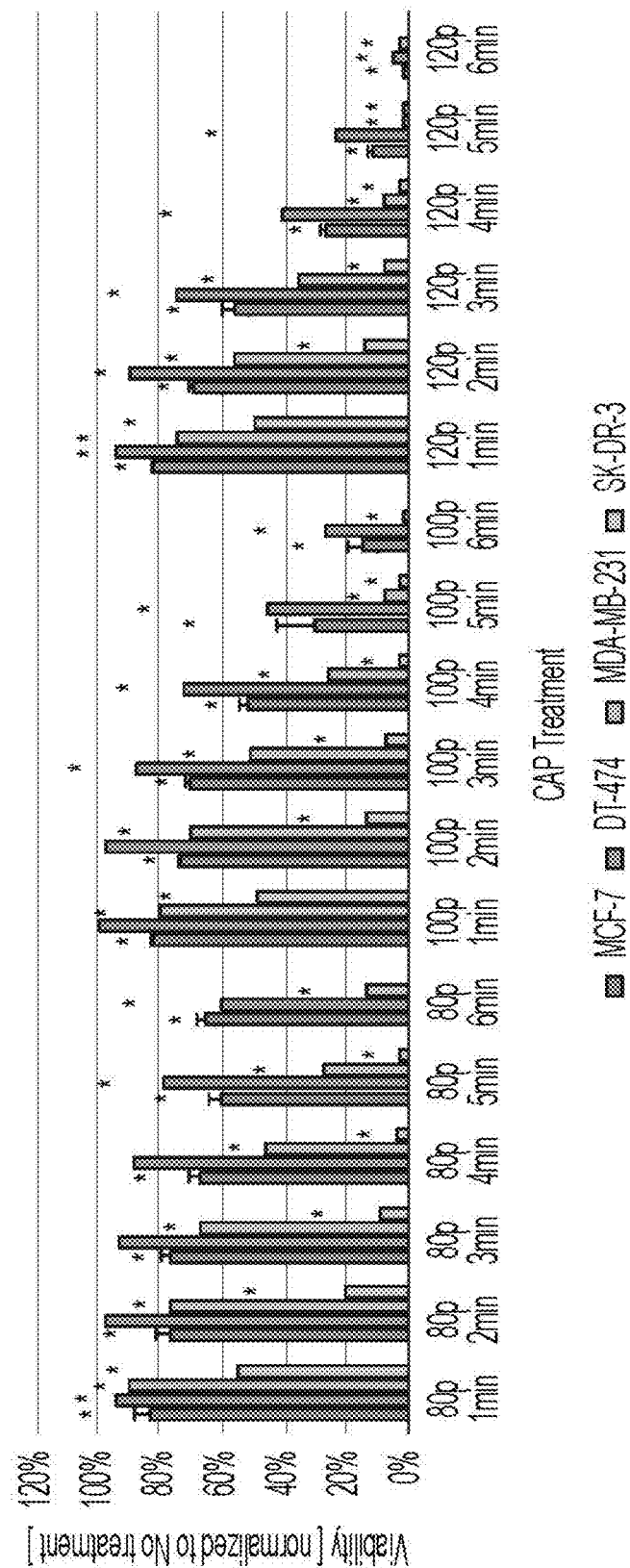
FIGS. 1A-1E show viability of breast cancer cell lines after CAP treatment with various power and time settings.
Figures 1B, 1C:
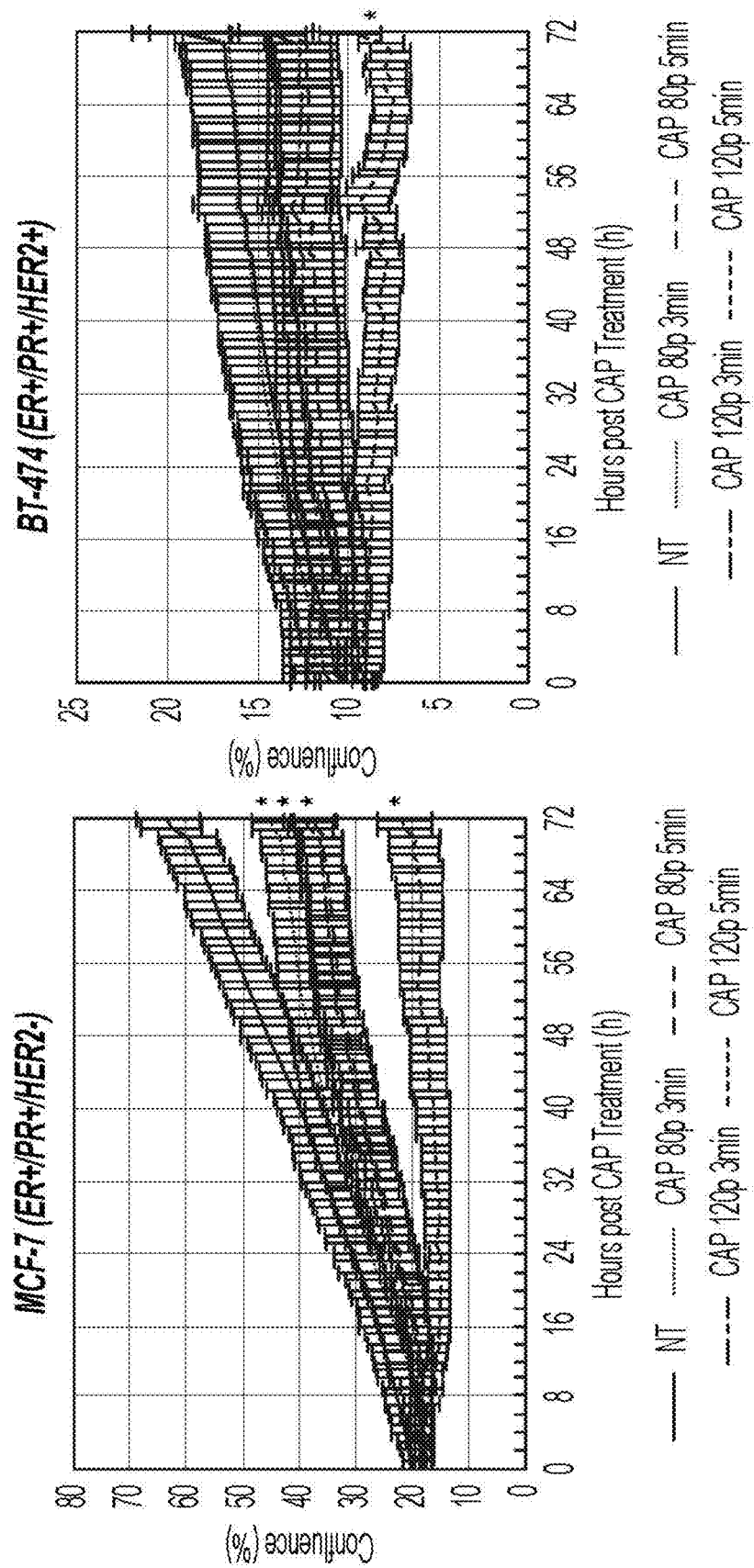
Figure 1E:
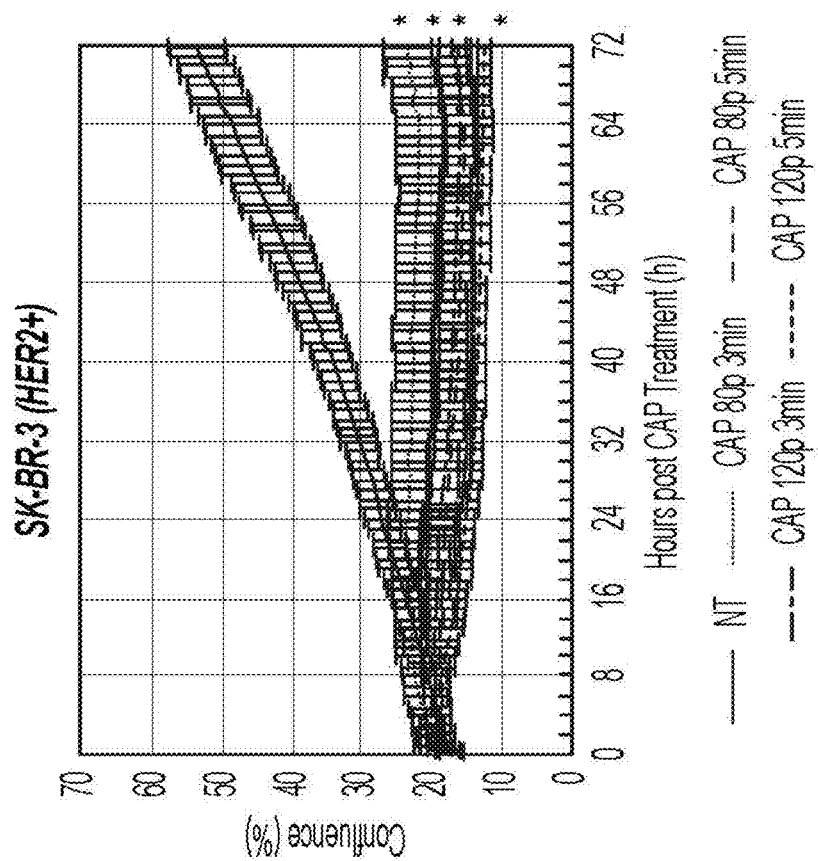
Figure 1D:
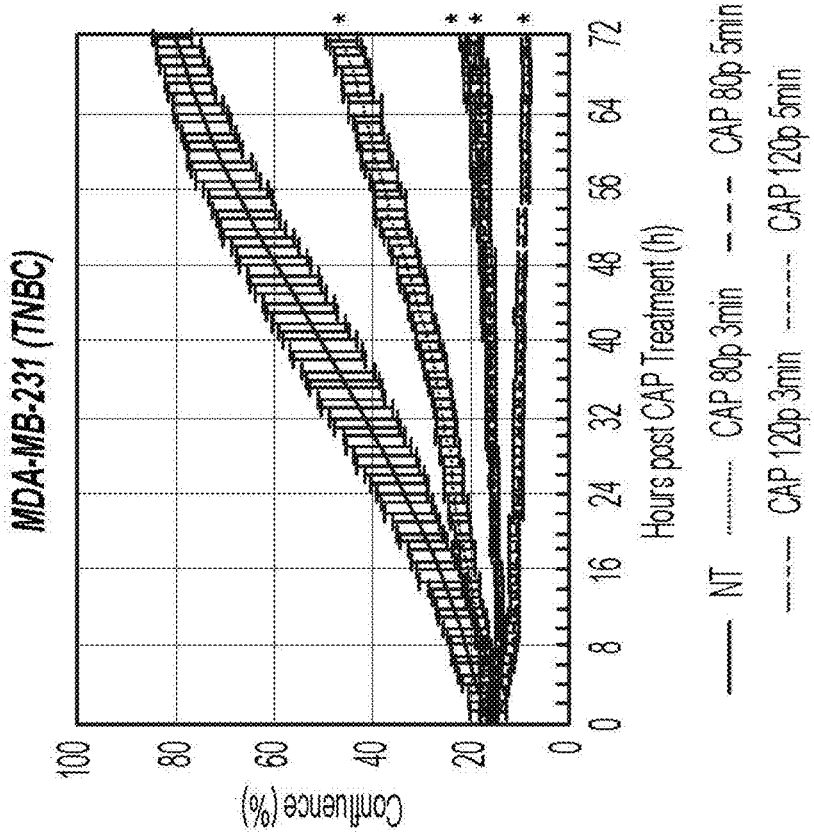

The present invention is described with reference to the drawings.

Viability and Proliferation Reduction of Breast Cancer Cells after Cold Plasma Treatment Previous studies have suggested that CAP has anti-cancer effect in various cell lines. Despite the wide range of cold plasma generating devices being used worldwide, emerging evidence has shown that cell type-specific resistance can be observed in tumor cells (Conway, G. E. et al. Non-thermal atmospheric plasma induces ROS-independent cell death in U373MG glioma cells and augments the cytotoxicity of temozolomide. Br J Cancer 114, 435-443 (2016)). In a previous study of CAP treatment on breast cancer cell lines, we reported that the cold plasma could reduce breast cancer cell viability up to 92-99% based on receptor status (Ly, L. et al. Canady cold plasma conversion system treatment: An effective inhibitor of cell viability in breast cancer molecular subtypes. Clinical Plasma Medicine (2020)). In developing the present invention, the sensitivity of four breast cancer cell lines with different receptor status were compared and their apoptosis and cell cycle progress were observed. All experiments were performed at the Jerome Canady Research Institute for Advanced Biological and Technological Sciences in Takoma Park, Maryland USA Power- and time-dependent reduction in cell viability and proliferation rate of the four breast cancer cell lines was shown in FIGS. 1A-1E. The viability of the cold plasma-treated cells was normalized to untreated cells 48-hour post cold plasma treatment. Increasing treatment time and power lead to lower cell viability across all 4 cell lines, among which SK-BR-3 ($ER^-PR^-HER2^+$) is the most sensitive to cold plasma treatment, and BT-474 ($ER^+PR^+HER2^+$) requires the strongest dosage. The viability established here provides an overview of each breast cancer subtype's reaction to cold plasma treatment under different settings. In the following experiments, four breast cancer cell lines were tested with 2 power settings (80 p and 120 p) for 3 treatment durations (3, 5, and 6 min) with helium flow rate set to 3 LPM.

Cells treated by cold plasma were incubated for 72 hours, then the confluence of the cells as an indicator for proliferation rate was analyzed and plotted by IncuCyte and shown in FIGS. B-1E. Student t test was performed on each treatment dosage and every hour post cold plasma treatment compared to NT, and * denotes statistical significance if $p<0.05$ during 48- to 72-hour post treatment. Compared to No Treatment (NT), cold plasma treatment reduced the growth of all cell lines to different extent based on the cell type and dosage. For BT-474 ($ER^+PR^+HER2^+$) cells FIG. 1C), only with the highest dosage (cold plasma treatment with higher power and time at 120 p 5 min) the cells started to show statistically significant decrease in confluence after 26 hours post treatment compared to NT. For MCF-7 ($ER^+PR^+HER2^-$), MDA-MB-231 (TNBC), and SK-BR-3 ($ER^-PR^-HER2^+$) cells FIGS. 1i, 1D and 1E), proliferation rate decreased in a cold plasma power- and time-dependent manner: cold plasma treatment significantly slowed down MCF-7 cell proliferation but did not completely eliminate cells and they tended to recover after 48 hours of treatment; MDA-MD-231 cells was more responding to low dose cold plasma-treatment compared to BT-474 and MCF-7, and the highest dosage (120 p 5 min) was able to completely eradicated the cells; for SK-BR-3 ($ER^-PR^-HER2^+$) cells FIG. 1E), all treatment dosage effectively stopped cell proliferation.

Cytotoxicity of cold plasma on breast cancer cell reducing cell proliferation was visualized by cell proliferation marker Ki-67. Differential Ki-67 expression can result in important therapeutic implications (Soliman, N. A. & Yussif, S. M. Ki-67 as a prognostic marker according to breast cancer molecular subtype. Cancer Biol Med 13, 496-504, doi: 10.20892/j.issn.2095-3941.2016.0066 (2016) and Inwald, E. C. et al. Ki-67 is a prognostic parameter in breast cancer patients: results of a large population-based cohort of a cancer registry. Breast Cancer Res Treat 139, 539-552, doi:10.1007/s10549-013-2560-8 (2013)). Breast cancer cells were treated with desired cold plasma dosages and Ki-67/DAPI co-staining was performed 6, 24, or 48 hours post cold plasma treatment.

For quantification, Ki-67-positive (Ki-67$^+$) cell count was used instead of Ki-67$^+$ cell percentage because the late apoptotic or dead were washed off during the staining process resulting in a false total cell count. Nuclei that were clearly in focus were outlined and its mean fluorescence intensity (MFI) of Ki-67 channel was recorded. The mean of Ki-67 MFI was calculated for each treatment group (5 images) including No Treatment and Isotype control. A Ki-67$^+$ cell was defined as its Ki-67 MFI was greater than the lowest mean of MFI of all groups other than Isotype control for each cell line.

In images produced, Ki-67 staining was remarkably brighter in cells with No Treatment or with lower dosages of cold plasma than those treated with higher dosages. In MCF-7 (ER$^+$PR$^+$HER2$^-$) No treatment samples, Ki-67 was seen throughout the nucleoplasma, and in most cases in co-localization with nucleoli. At low dose or short incubation time (6 h 120 p 3 min, 6 h 120 p 5 min, 24 h 120 p 3 min, and 48 h 120 p 3 min), nucleoli were intact and Ki-67 expression was still observed but in less cells; at high dose (24 h 120 p 5 min and 48 h 120 p 5 min), Ki-67 staining was either diminished or presented throughout the nuclei with disrupted nucleoli. The same pattern was seen in all 4 breast cancer cell lines with slightly different treatment conditions. For MCF-7 (ER$^+$PR$^+$HER2$^-$), BT-474 (ER$^+$PR$^+$HER2$^+$), and MDA-MB-231 (TN), cold plasma treatment at 120 p 5 min caused visual damage to the nuclei after 24-hour incubation. For SK-BR-3 (HER2$^+$), visual nuclear damage was observed as early as 6-hour post cold plasma treatment at a lower treatment dose of 80 p 3 min.

The number of Ki-67$^+$ cells was reduced by cold plasma treatment in all 4 breast cancer cell lines as a power- and time-dependent manner. Over 6, 24, and 48 h incubation post cold plasma treatment, the Ki-67$^+$ cell number gradually decreased. In addition to the reduced Ki-67$^+$ cell count, the shape and size of the nuclei changed after cold plasma treatment. Shrinkage and fragmentation were seen in all the cells treated with the highest dosage of cold plasma. The reduction in cell number correlates with the inhibition of growth observed in the viability and confluency.

Apoptosis of Breast Cancer Cells after Cold Plasma Treatment

Figure 2:
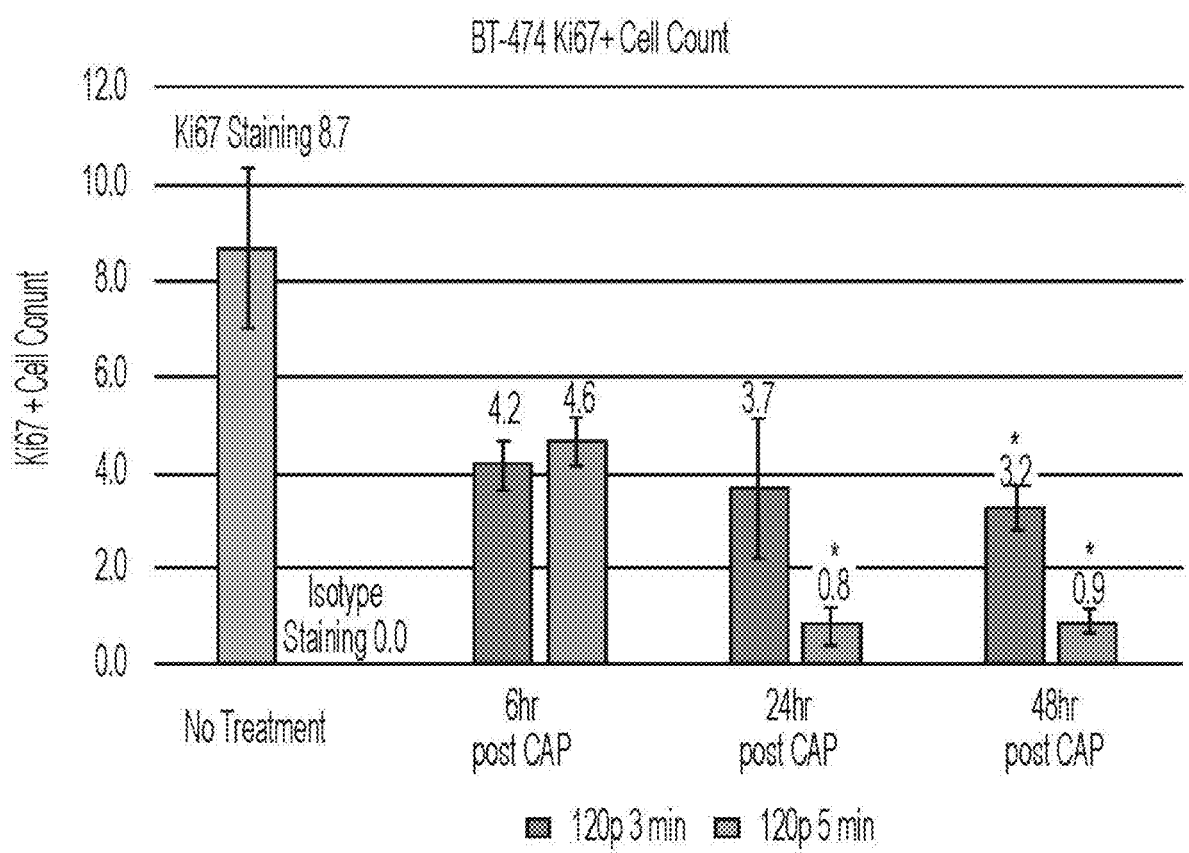
FIG. 2 shows Ki67 staining of MCF-7 ($ER^+PR^+HER2^-$) cell line. Averaged quantification plot of 'Ki67$^+$' cell count of MCF-7 cells 6/24/48 h post CAP treatment (* above the bars denotes statistical significance of CAP treated group compared to No Treatment group. *p<0.05).
Figure 3:
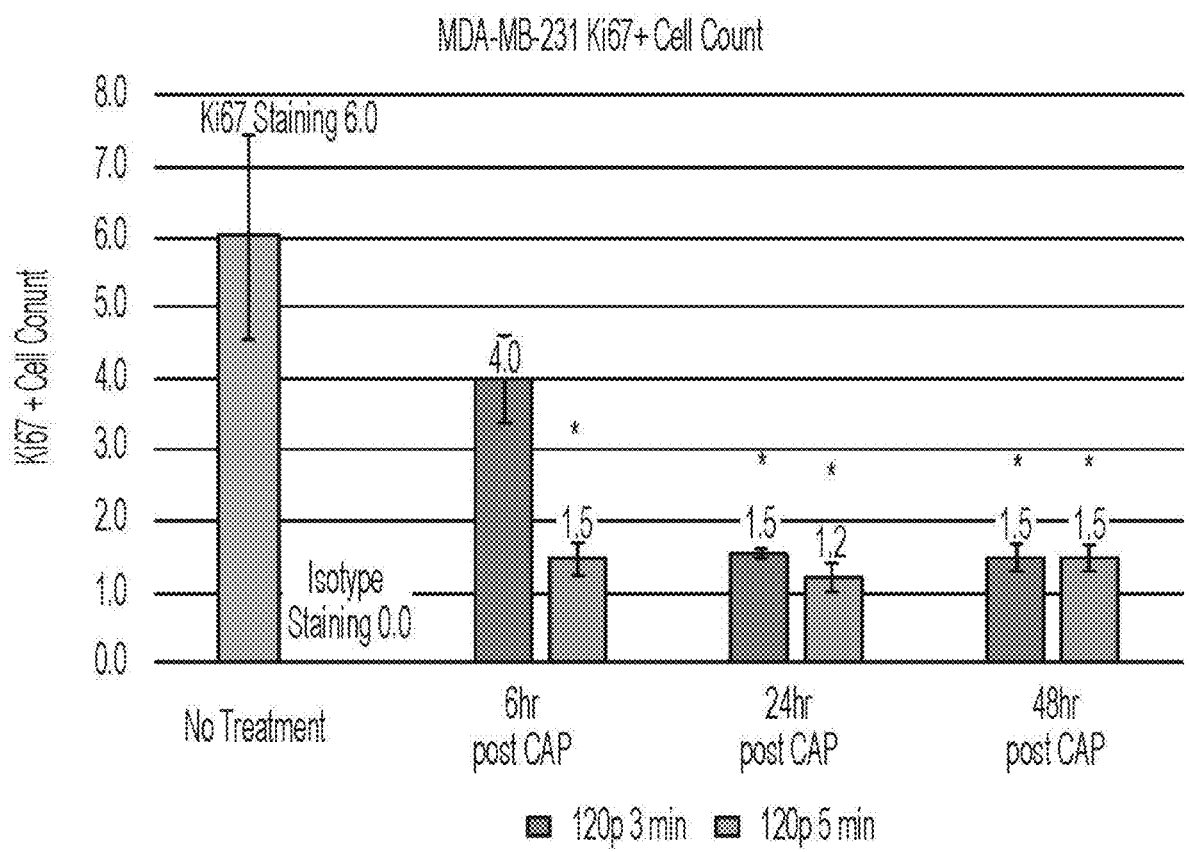
FIG. 3 shows Ki67 staining of BT-474 ($ER^+PR^+HER2^+$) cell line. Averaged quantification plot of 'Ki67$^+$' cell count of BT-474 cells 6/24/48 h post CAP treatment (* above the bars denotes statistical significance of CAP treated group compared to No Treatment group. *p<0.05).
Figure 4:
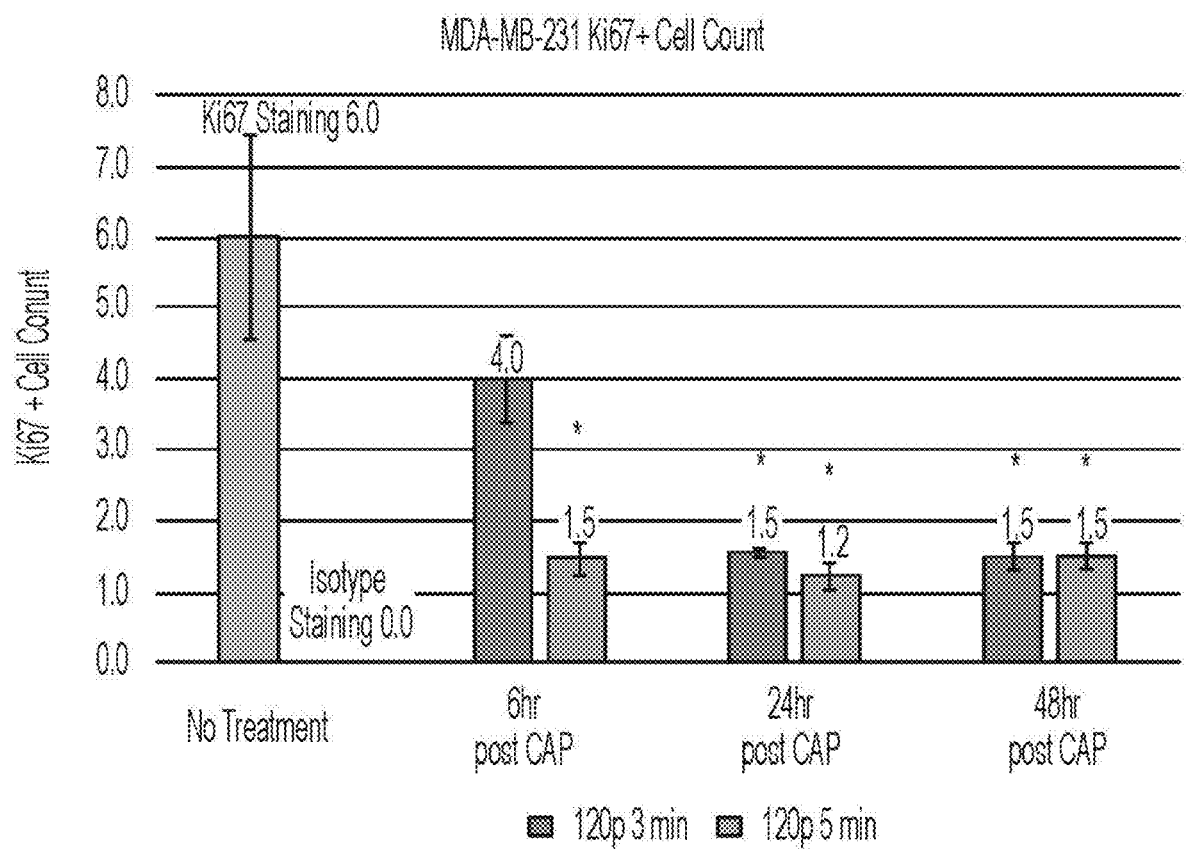
FIG. 4 shows Ki67 staining of MDA-MB-231 (TN) cell line. Averaged quantification plot of 'Ki67$^+$' cell count of MDA-MB-231 cells 6/24/48 h post CAP treatment (* above the bars denotes statistical significance of CAP treated group compared to No Treatment group. *p<0.05).
Figure 5:
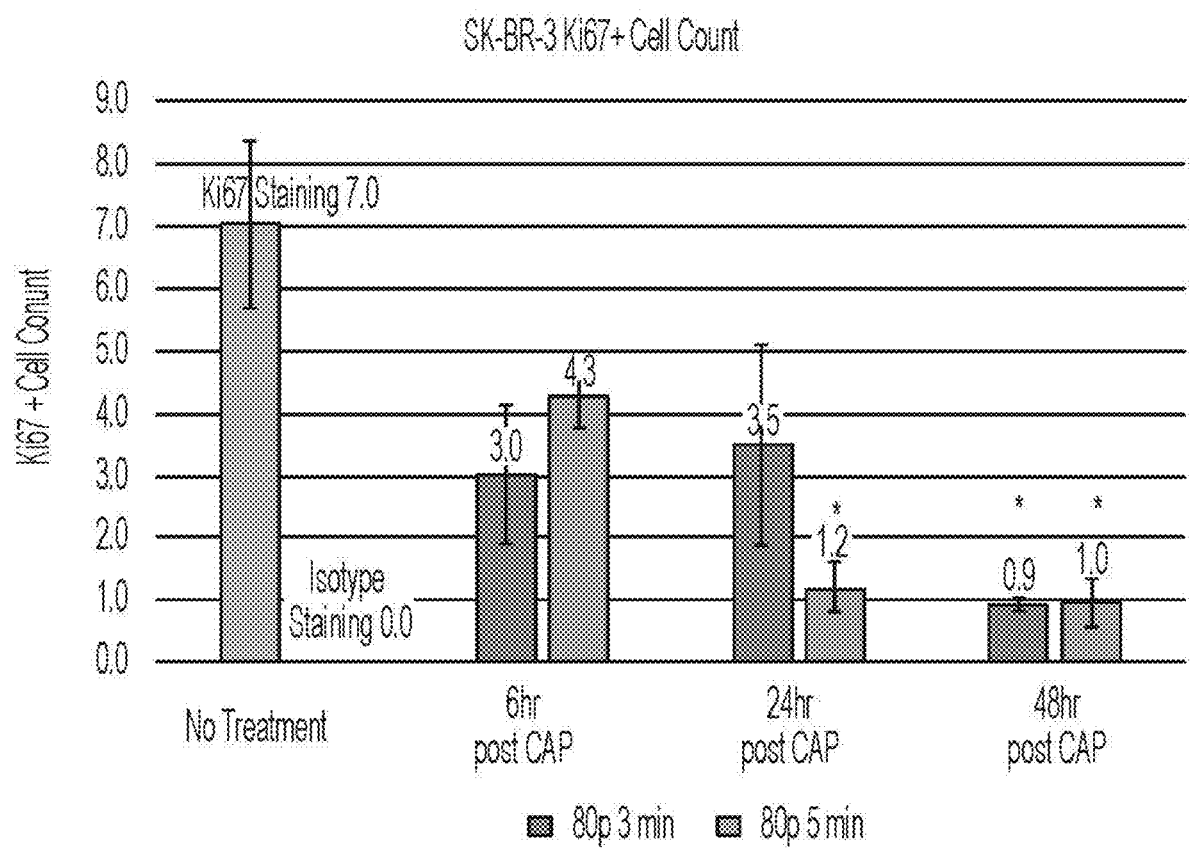
FIG. 5 shows Ki67 staining of SK-BR-3 ($HER2^+$) cell line. Averaged quantification plot of 'Ki67$^+$' cell count of SK-BR-3 cells 6/24/48 h post CAP treatment (* above the bars denotes statistical significance of CAP treated group compared to No Treatment group. *p<0.05).
Figure 6A:
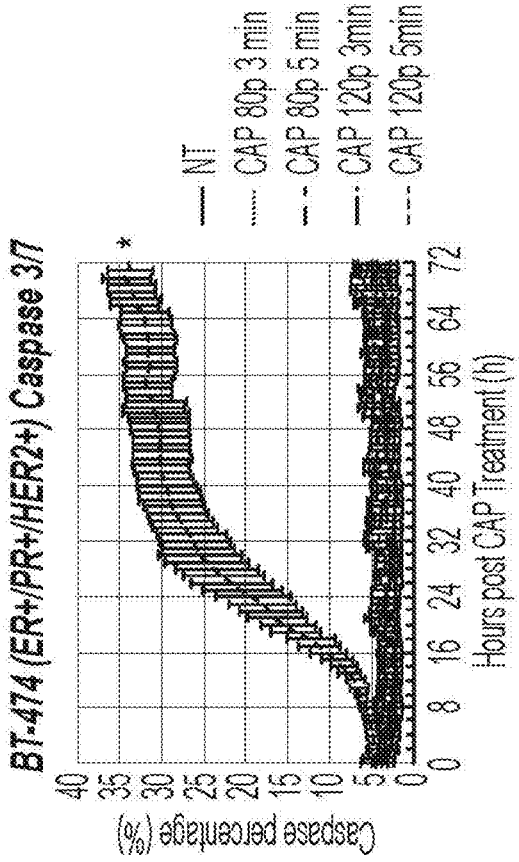
FIG. 6 shows Caspase 3/7 activity of breast cancer cell lines with or without CAP treatment over 72 hours A) MCF-7 ($ER^+PR^+HER2^-$). B) BT-474 ($ER^+PR^+HER2^+$). C) MDA-MB-231 (TN). D) SK-BR-3 ($HER2^+$).
Figure 6B:
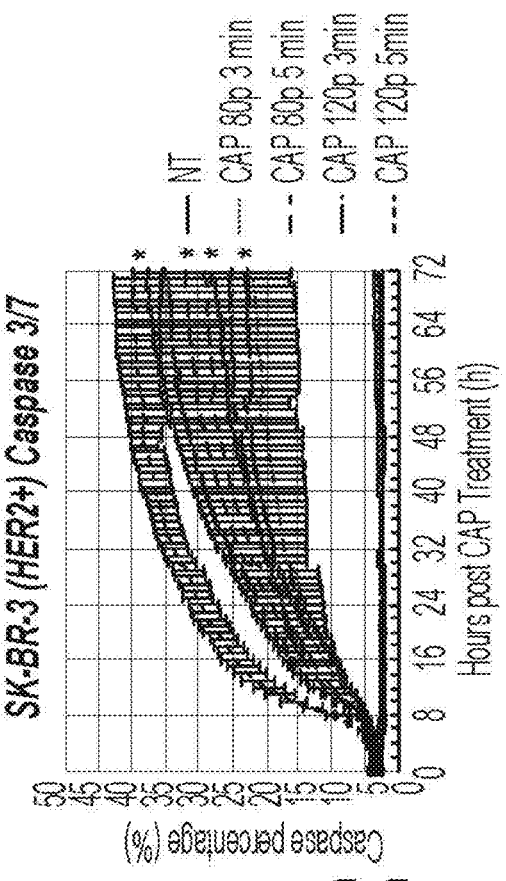
Figure 6C:
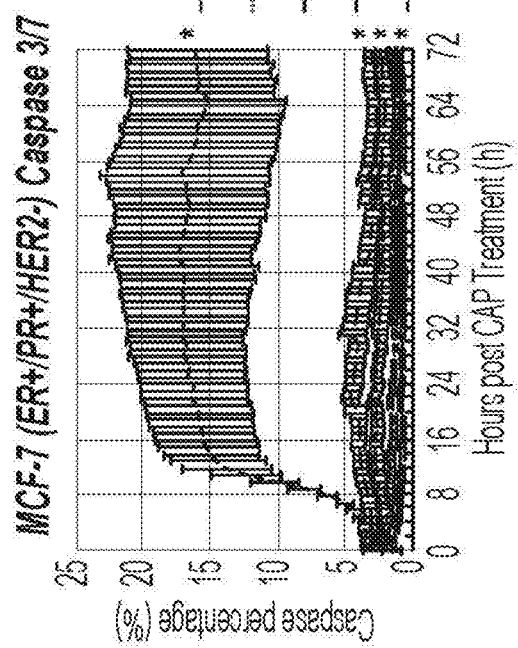
Figure 6D:
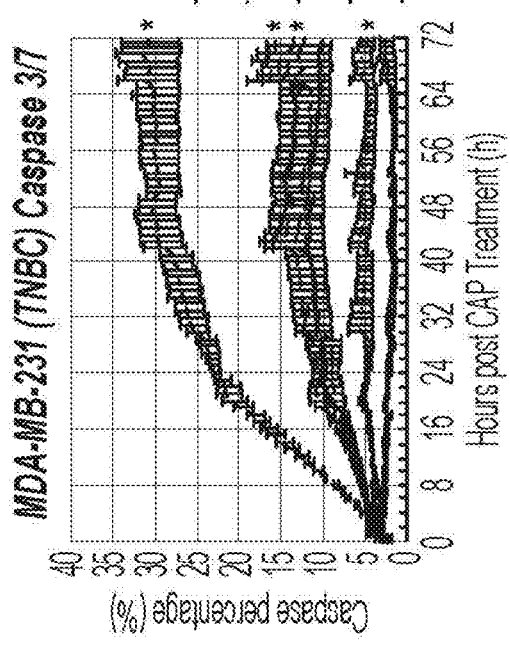

The next question was whether cold plasma merely reduced cell proliferation or induced cell death. As an important step of downstream apoptosis pathway, caspase 3/7 activity was measured to understand the timeline of apoptotic activities for each cell line. After cold plasma treatment, cells were stained with IncuCyte® Caspase-3/7 Dyes for Apoptosis, put back immediately back to incubator and scanned with IncuCyte 10× lens for 3 days (0 to 72 hours post cold plasma). Phase contrast images were taken every 1 hour to monitor the progress of apoptosis. The percentage of caspase-3/7-active cells out of the total population per image from 0 to 72 hours post cold plasma treatment was analyzed by IncuCyte software and shown in FIG. 2.

For all four breast cancer cell lines, apoptosis (if induced by cold plasma) initiated within 4 hours post treatment and plateaued after 48 hours post treatment. For each cell line, the slope of the caspase 3/7 curve representing the kinetic of apoptotic activity is dose-dependent, suggesting that the higher cold plasma dose (higher power or longer duration), the earlier and faster apoptosis occurred.

The great advantage of IncuCyte live cell imaging is to monitor and visualize apoptosis progress continuously from Hour 0. However, the limitation of IncuCyte, as is to all 2-dimensional imaging analysis, is that the detached cells were not in the focal plane thus not in the analysis. To better quantify the apoptotic population and calculate the percentage of apoptosis, cells were stained with Annexin V vs. Propidium iodide (PI) staining and cell apoptosis at 24 and 48 post cold plasma treatment was confirmed by flow cytometry. Representative scatter and quantification plots of 'live', 'early apoptosis', and 'late apoptosis/dead' cells for each breast cancer cell line were shown in FIGS. 7A-10B.

For all four cell lines, in the No Treatment samples, the majority of cells (~80-90%) of cells were viable ('Live', Annexin V$^-$/PI$^-$). In contrast, exposure to cold plasma treatment for 3, 5 or 6 min at 80 p or 120 p induced apoptosis to various extent over 24 and 48 hr incubation time.

Figure 7A:
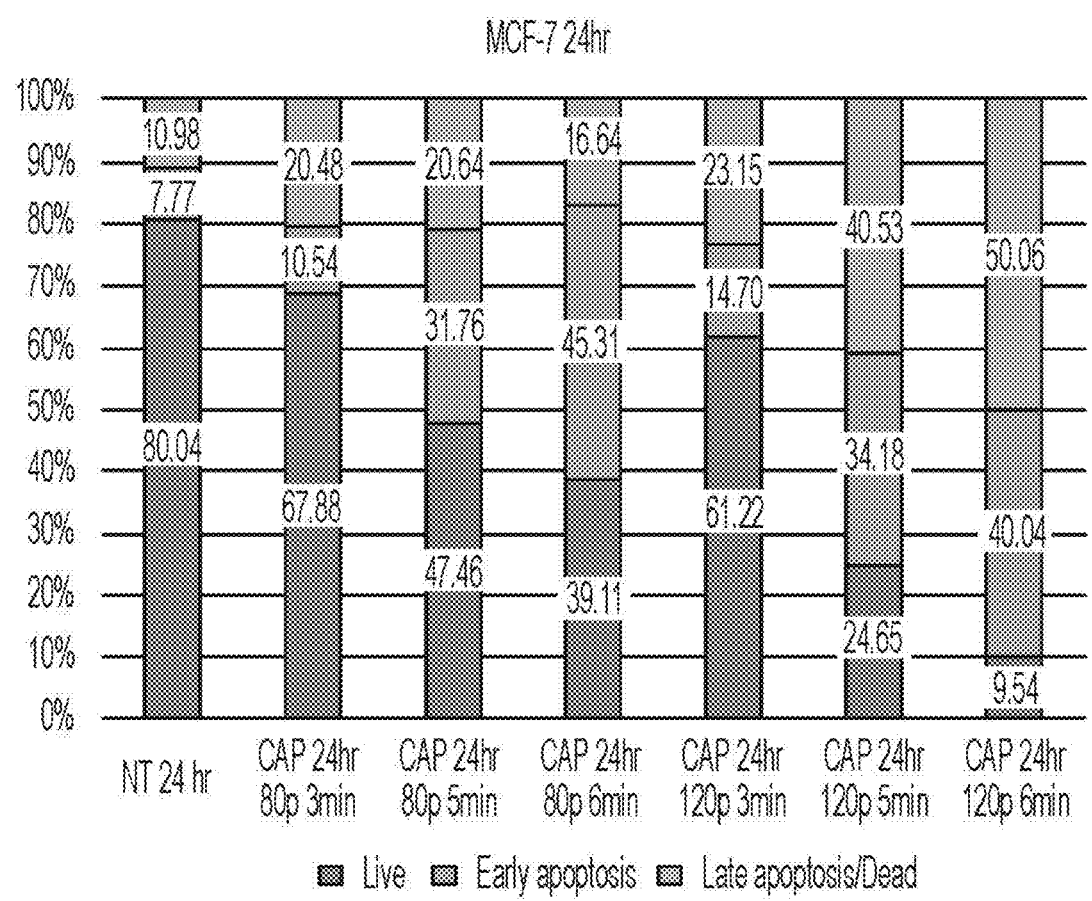
FIGS. 7A and 7B show apoptosis analyses of an MCF-7 ($ER^+PR^+HER2^-$) cell line.
Figure 7B:
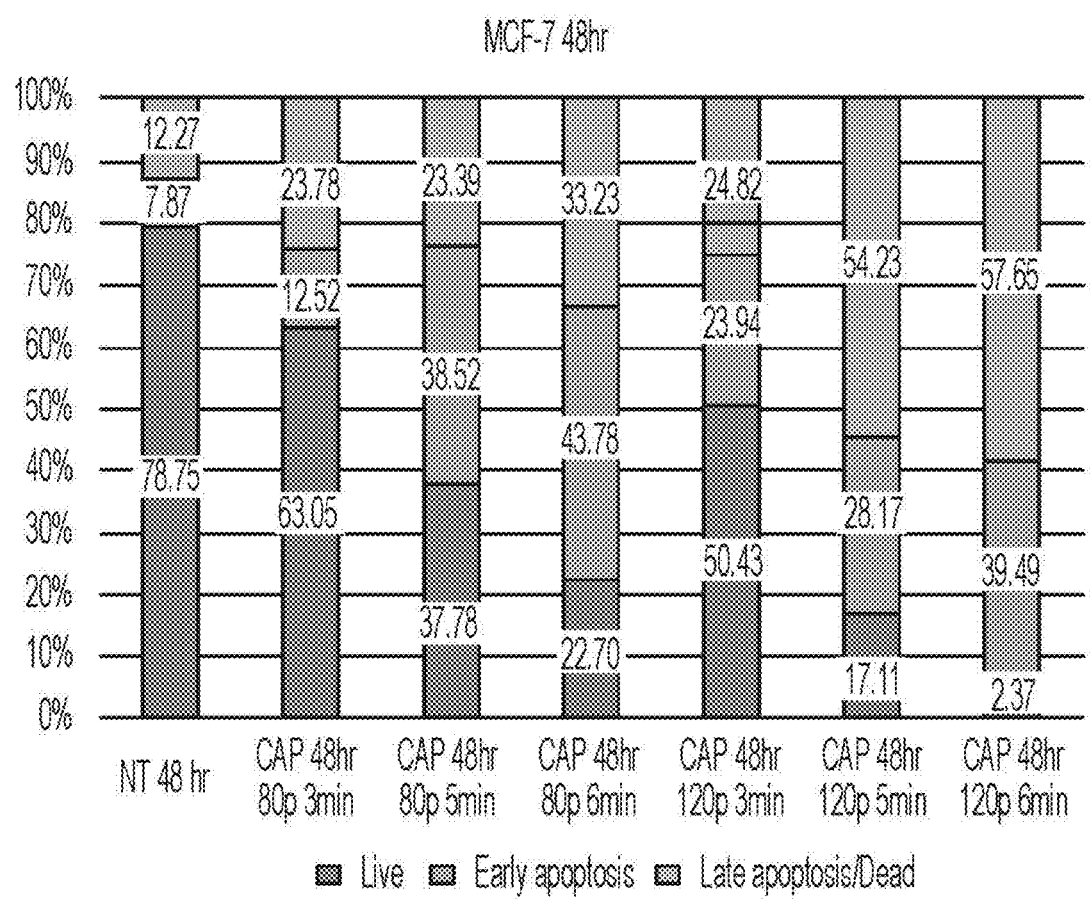
Figure 8A:
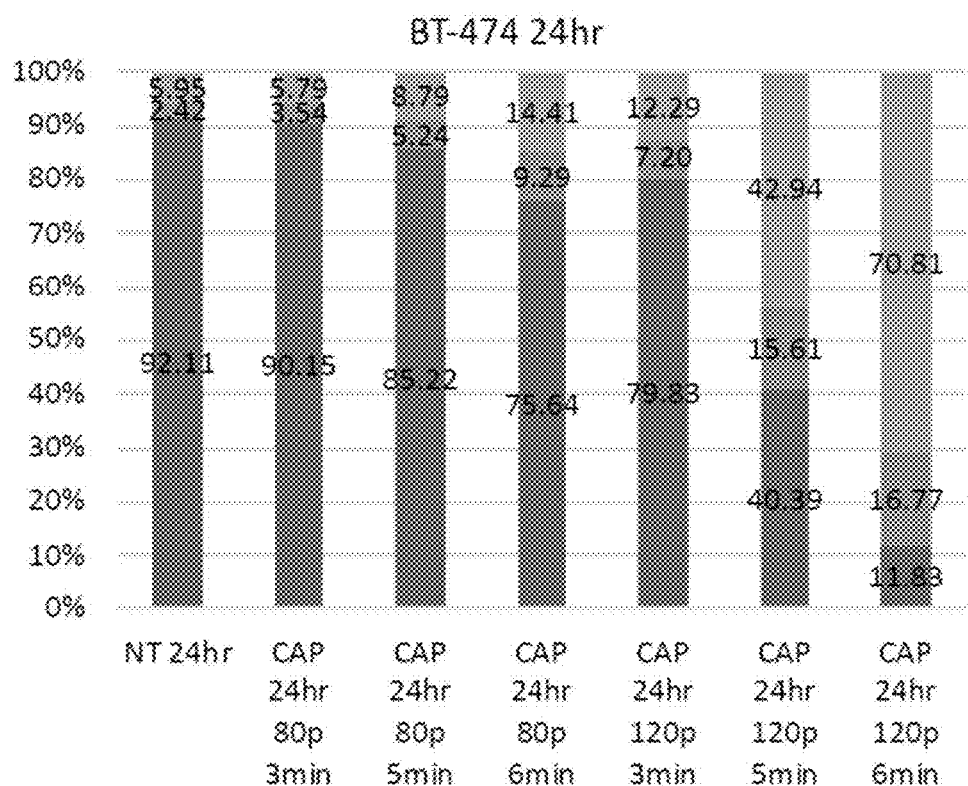
FIGS. 8A and 8B show apoptosis analyses of a BT-474 ($ER^+PR^+HER2^+$) cell line.
Figure 8B:
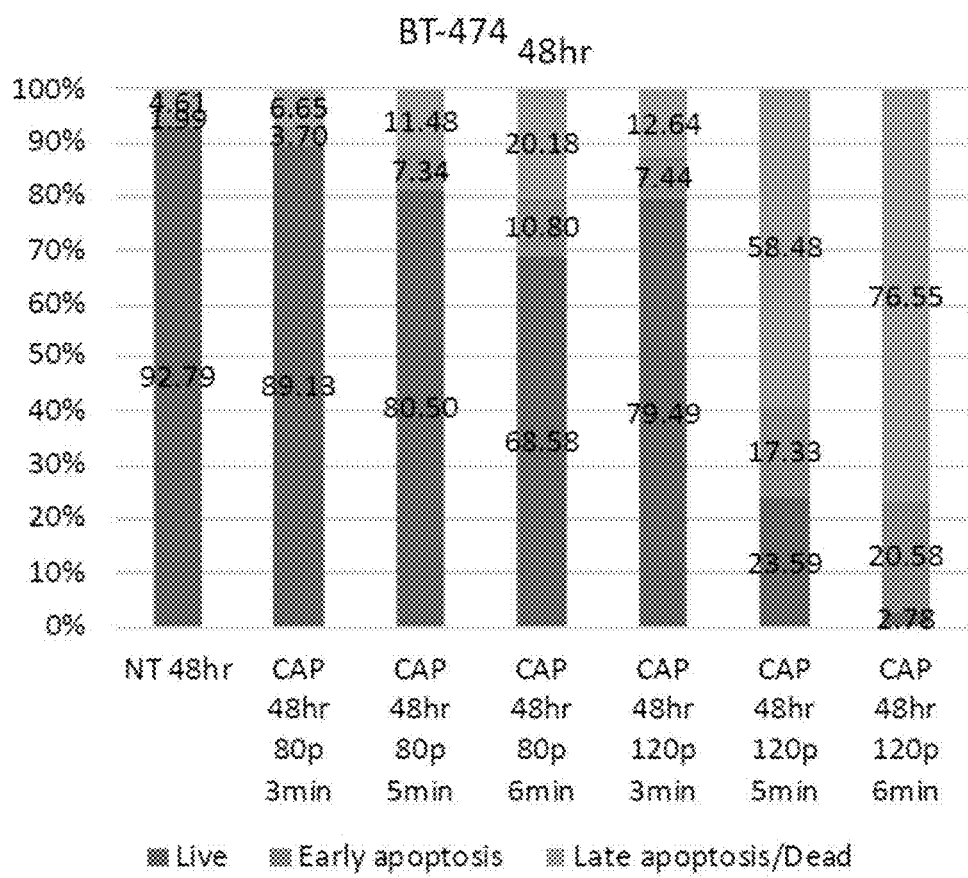
Figure 9A:
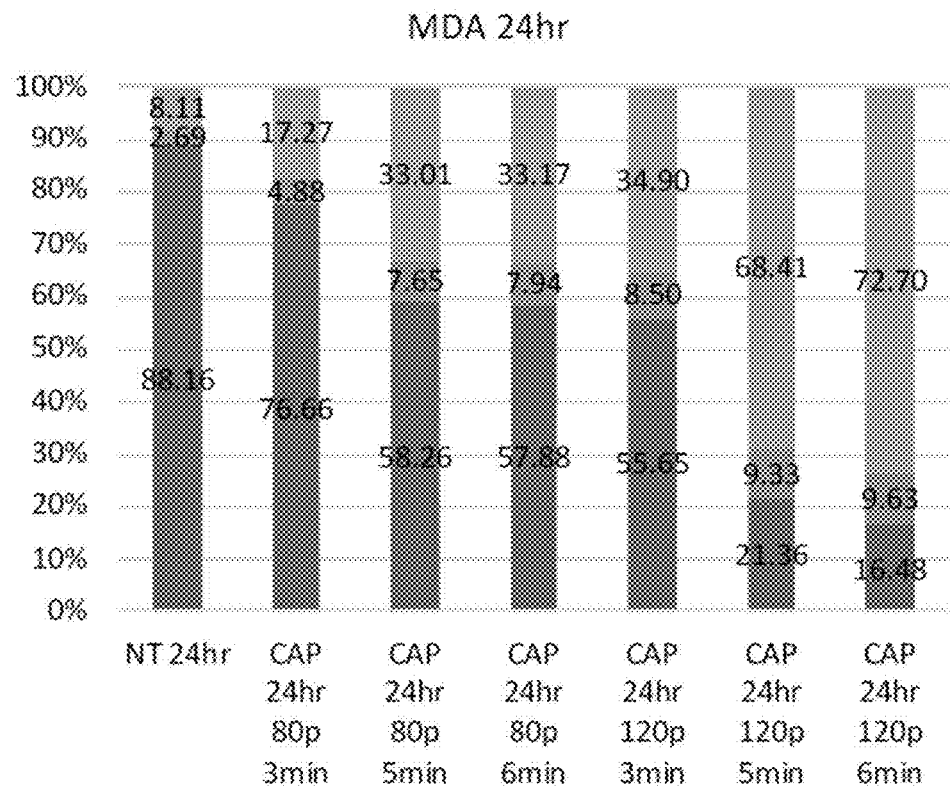
FIGS. 9A-9B show the results of an apoptosis analysis of MDA-MB-231 (TN) cell line.
Figure 9B:
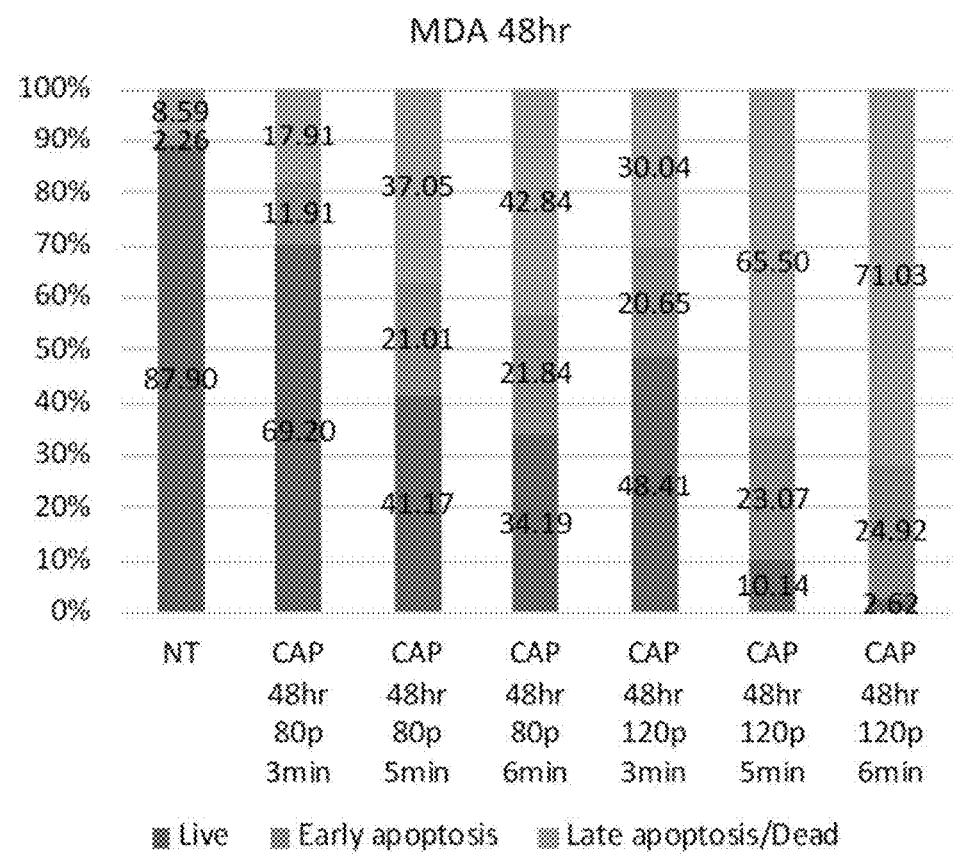
Figure 10A:
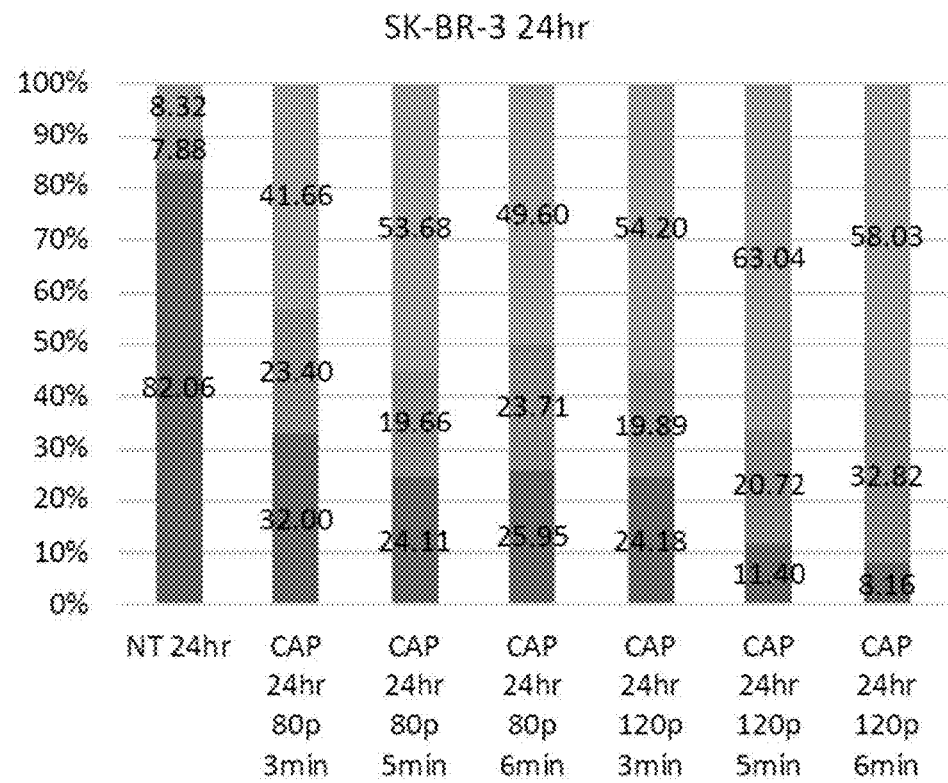
FIGS. 10A-10B show the results of an apoptosis analysis of SK-BR-3 ($HER2^+$) cell line.
Figure 10B:
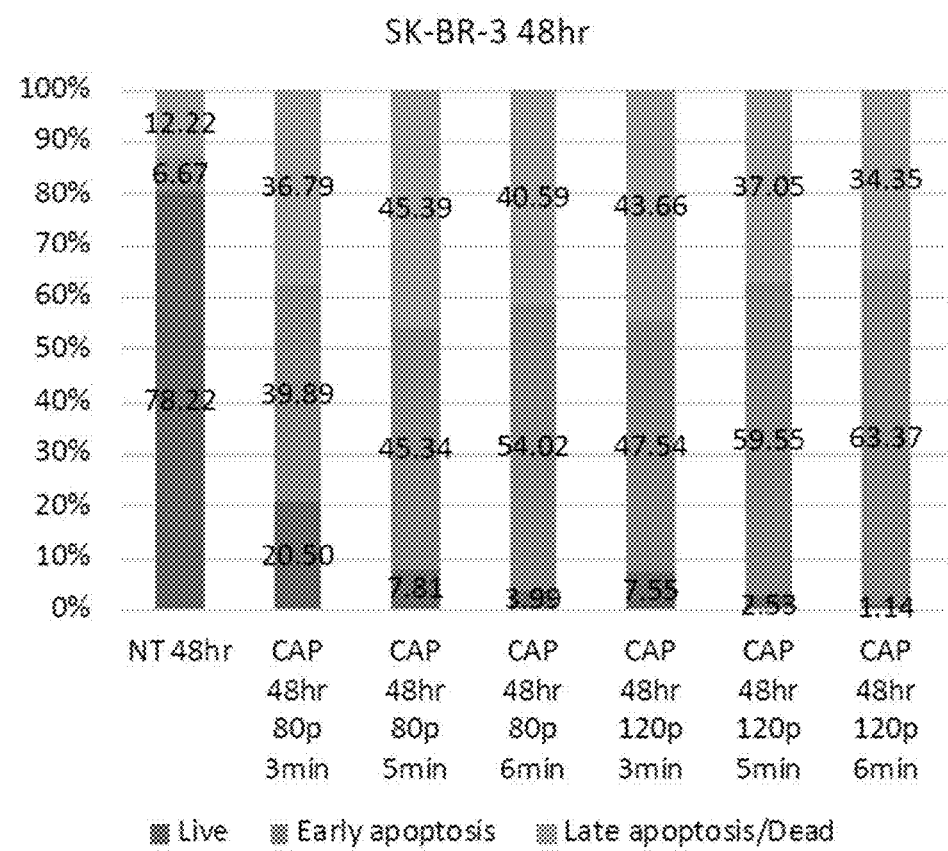

The population of 'Live' cells significantly decreased with increasing treatment power and time compared to No Treatment (p value ranges from <0.05 to <0.001). MCF-7 (ER$^+$PR$^+$HER2$^-$) 'Live' population decreased from 80.04% to 2.37% after cold plasma treatment (FIGS. 7A and 7B); BT-474 (ER$^+$PR$^+$HER2$^+$) 'Live' population decreased from 92.11% to 2.78% after cold plasma treatment (FIGS. 8A and 8B); MDA-MB-231 (TN) 'Live' population decreased from 88.16% to 2.62% after cold plasma treatment (FIGS. 9A and 9B); SK-BR-3 (HER2$^+$) 'Live' population decreased from 82.06% to 1.14% after cold plasma treatment (FIGS. 10A and 10B). With increasing treatment power and time, the increase in cells undergoing early apoptosis was seen in all 4 cell lines.

In addition, SK-BR-3 (HER2$^+$) cells were the most susceptible to cold plasma treatment, and BT-474 (ER$^+$PR$^+$HER2$^+$) cells were the most resistance among the 4 cell lines. Strong statistically significant different (***p<0.001) 'live' population was observed 24 hours post cold plasma treatment in SK-BR-3 (HER2$^+$) (FIG. 10A) with the lowest treatment dosage (80 p 3 min). BT-474 (ER$^+$PR$^+$HER2$^+$) did not show significant decrease until 24 hours with cold plasma treatment at 80 p for 6 min (*p<0.05, FIG. 8A) or 48 hours with cold plasma treatment at 80 p for 5 min (*p<0.05, FIG. 8B). This finding matches the viability and proliferation inhibition described above.

Comparing the population of 48 hr (FIGS. 7A, 8A, 9A, and 10A)) to 24 hr post cold plasma treatment (FIGS. 7B, 8B, 9B and 10B, respectively), cold plasma-induced apoptosis could take up to 48 hours. For example, at 80 p for 3 and 6 min, MCF-7 (ER$^+$PR$^+$HER2$^-$) showed an increase in apoptotic cell population from 32.17% to 60.89% 24 hr post cold plasma treatment; and from 36.95% to 87.30% for 48 hr post cold plasma treatment, indicating that more cells entered apoptosis procedure between 24 and 48 hours. This phenomenon can be observed in all 4 cell lines for all cold plasma treatment conditions.

Temporal Progress of Cell Cycle

3 Stable cell populations for breast cancer cell lines were generated with the IncuCyte® Cell Cycle Green/Red Lentivirus Reagent and treated with cold plasma for desired dosages. There was a technical difficulty when generating a stable cell population for HER2$^+$ subtype SK-BR-3. Attempt was made with another HER2$^+$ cell line AU-565, but it also failed to produce a stable cell line with the IncuCyte® Cell Cycle Green/Red Lentivirus Reagent. Therefore cell cycle analysis was not performed on HER2$^+$ subtype.

After cold plasma treatment, cells were monitored in the IncuCyte® for 3 days. Quantification data and phase contrast images for cells in G1 (Red) or S/G2/M (Green) or S to G1 transition (S-G1, Yellow) phases are shown in FIG. 11 to FIG. 13 and FIGS. 22 to 24.

Figure 22:
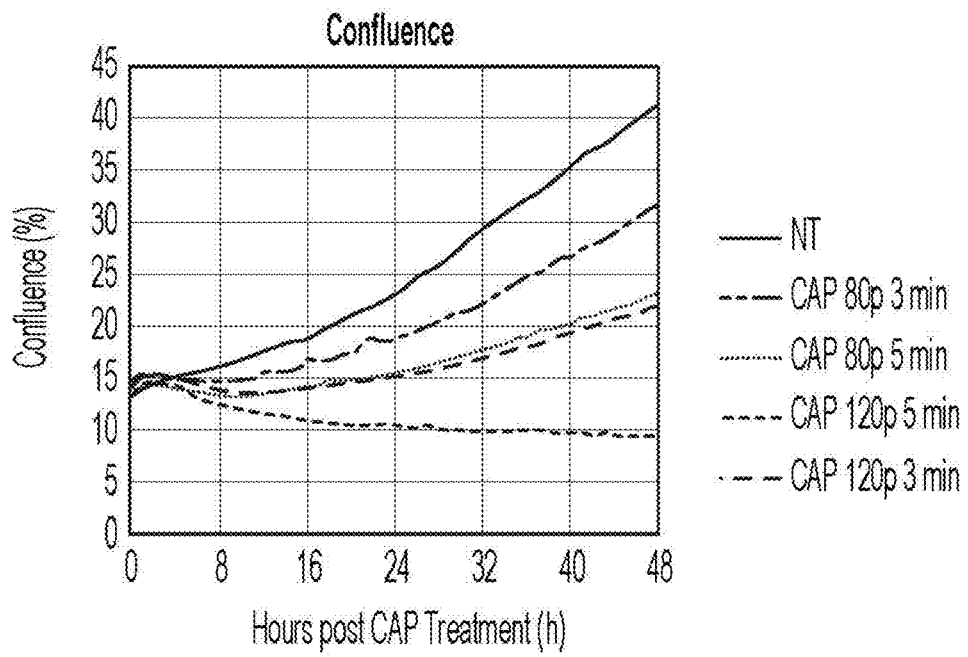
FIG. 22 shows cell cycle of MCF-7 ($ER^+PR^+HER2^-$) stable cell line generated with IncuCyte® Cell Cycle Green/Red Lentivirus Reagent untreated or treated by CAP at 80 p or 120 p for 3 min or 5 min. Confluence of cells 0-48 hours post treatment.
Figure 23:
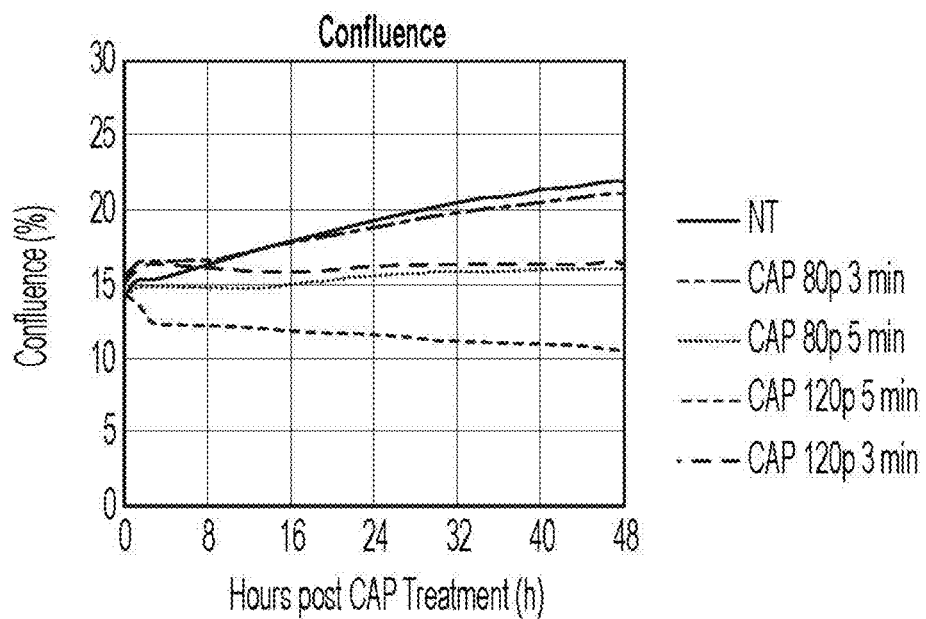
FIG. 23 shows cell cycle of BT-474 ($ER^+PR^+HER2^+$) stable cell line generated with IncuCyte® Cell Cycle Green/Red Lentivirus Reagent untreated or treated by CAP at 80 p or 120 p for 3 min or 5 min. Confluence of cells 0-48 hours post treatment.
Figure 24:
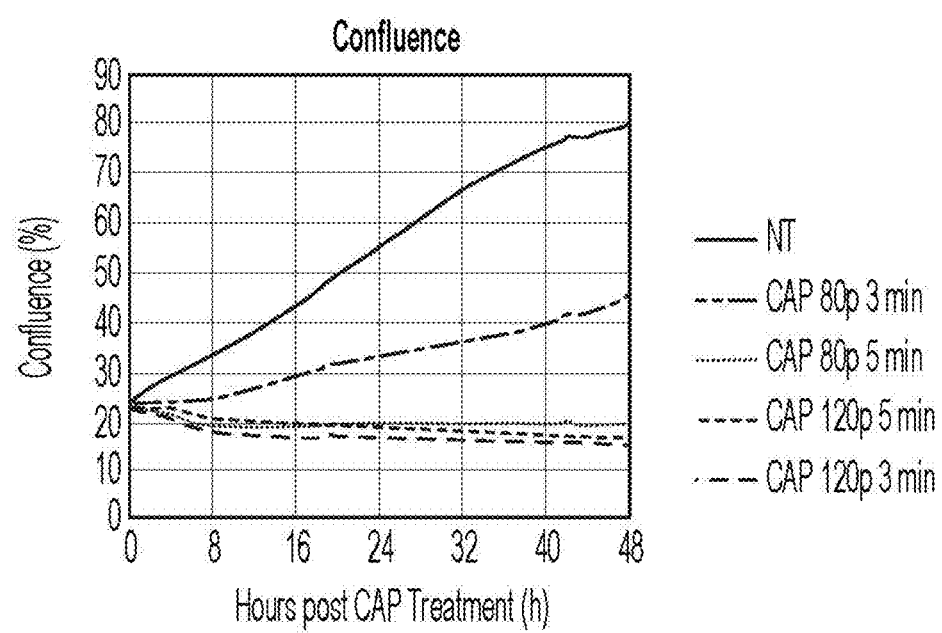
FIG. 24 is a graph of the confluence of cells 0-48 hours post treatment for cell cycle of MDA-MB-231 (TNBC) stable cell line generated with IncuCyte® Cell Cycle Green/Red Lentivirus Reagent untreated or treated by CAP at 80 p or 120 p for 3 min or 5 min.

Confluence of the stable cell lines after cold plasma-treatment shown in FIGS. 22 to 24 consistent with the confluence of non-transfected cell lines (FIGS. 1B-1D) confirmed the cell function was not altered by the lentivirus.

Figure 11:
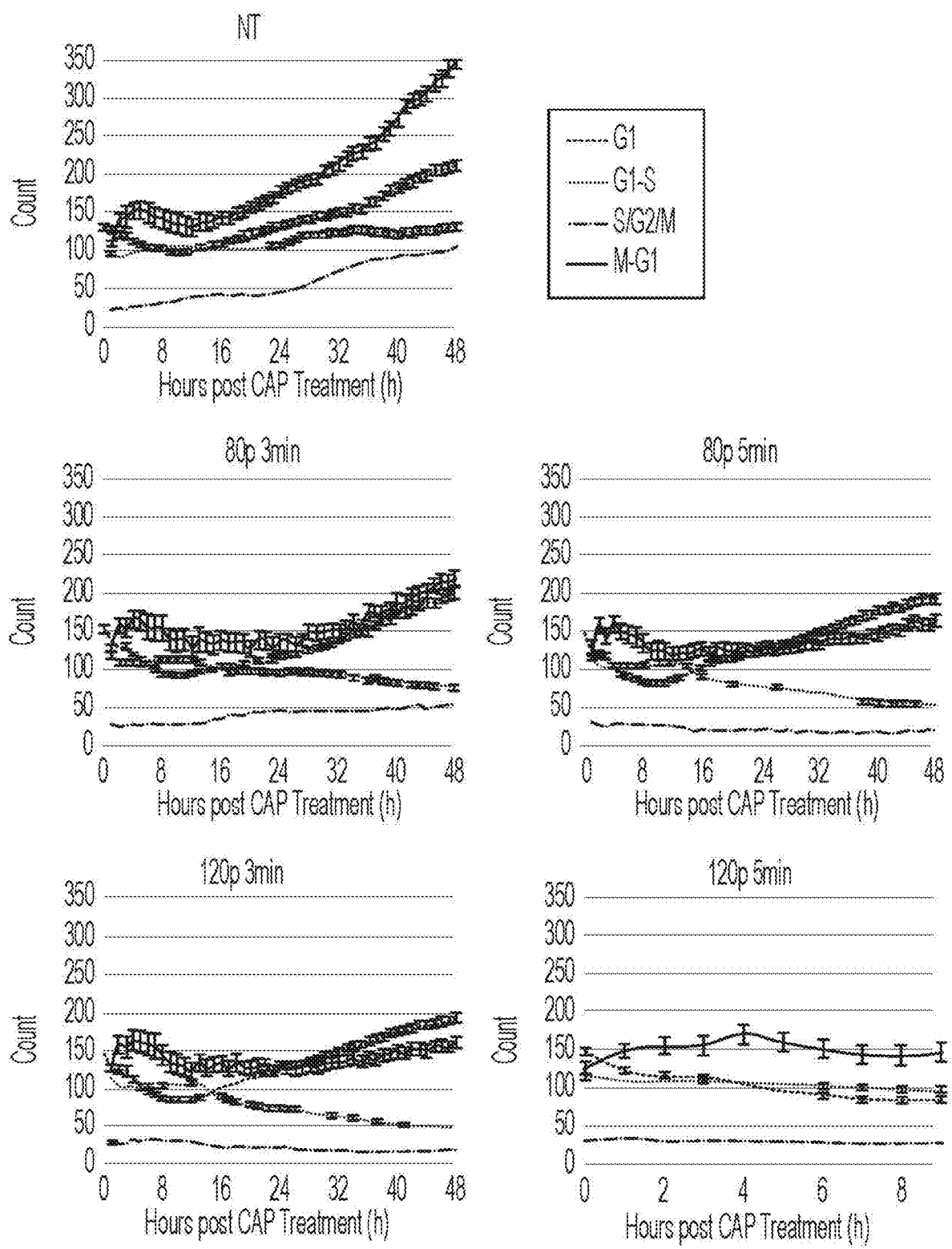
FIG. 11 shows quantification of MCF-7 ($ER^+PR^+HER2^-$) cells in G1, G1-S, S/G2/M, and M-G1 phases over 72 hours after CAP treatment. A-E) Cells were untreated or treated by CAP with various dosage.
Figure 12:
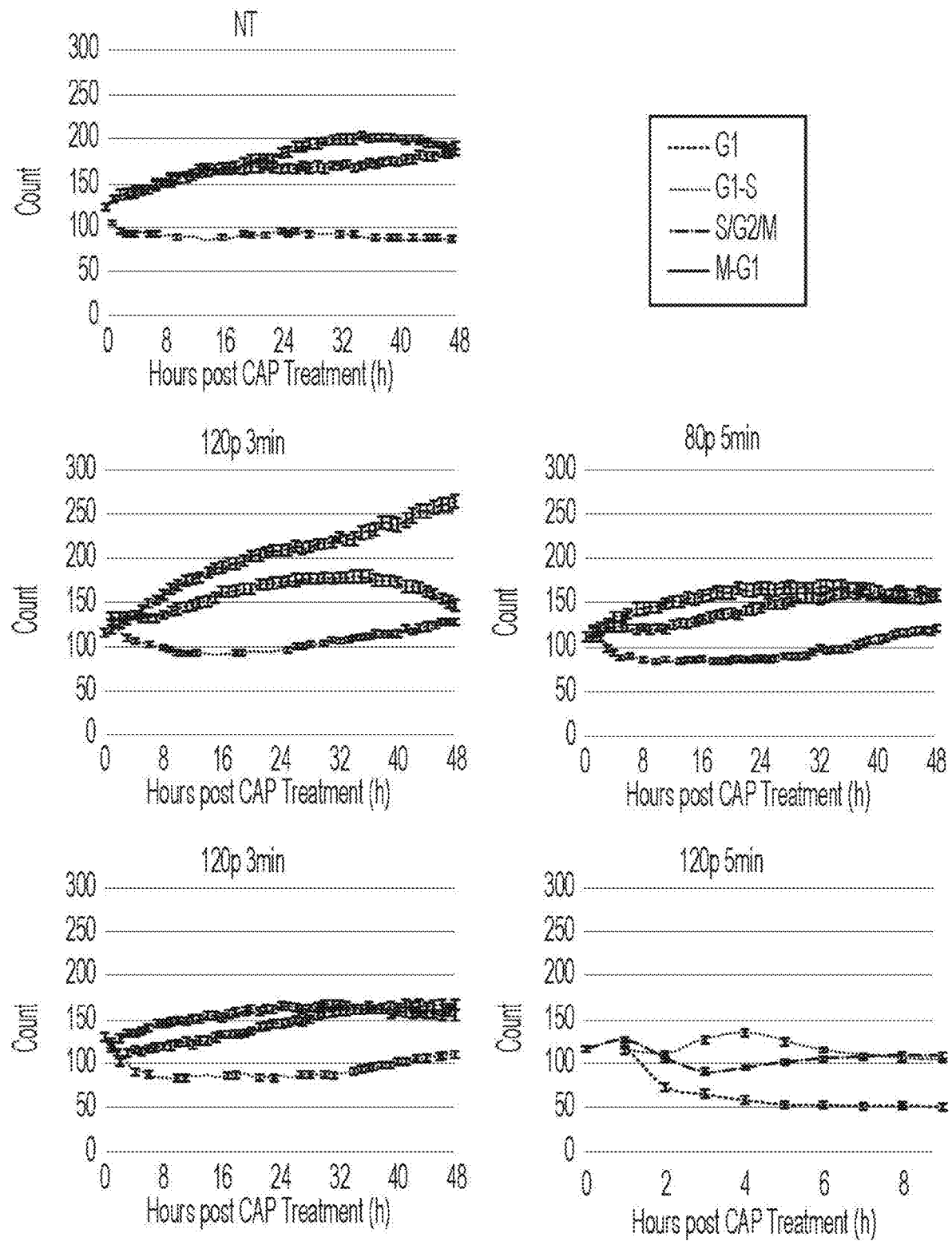
FIG. 12 shows quantification of BT-474 ($ER^+PR^+HER2^+$) cells in G1, G1-S, S/G2/M, and M-G1 phases over 72 hours after CAP treatment. A-E) Cells were untreated or treated by CAP with various dosage.
Figure 13:
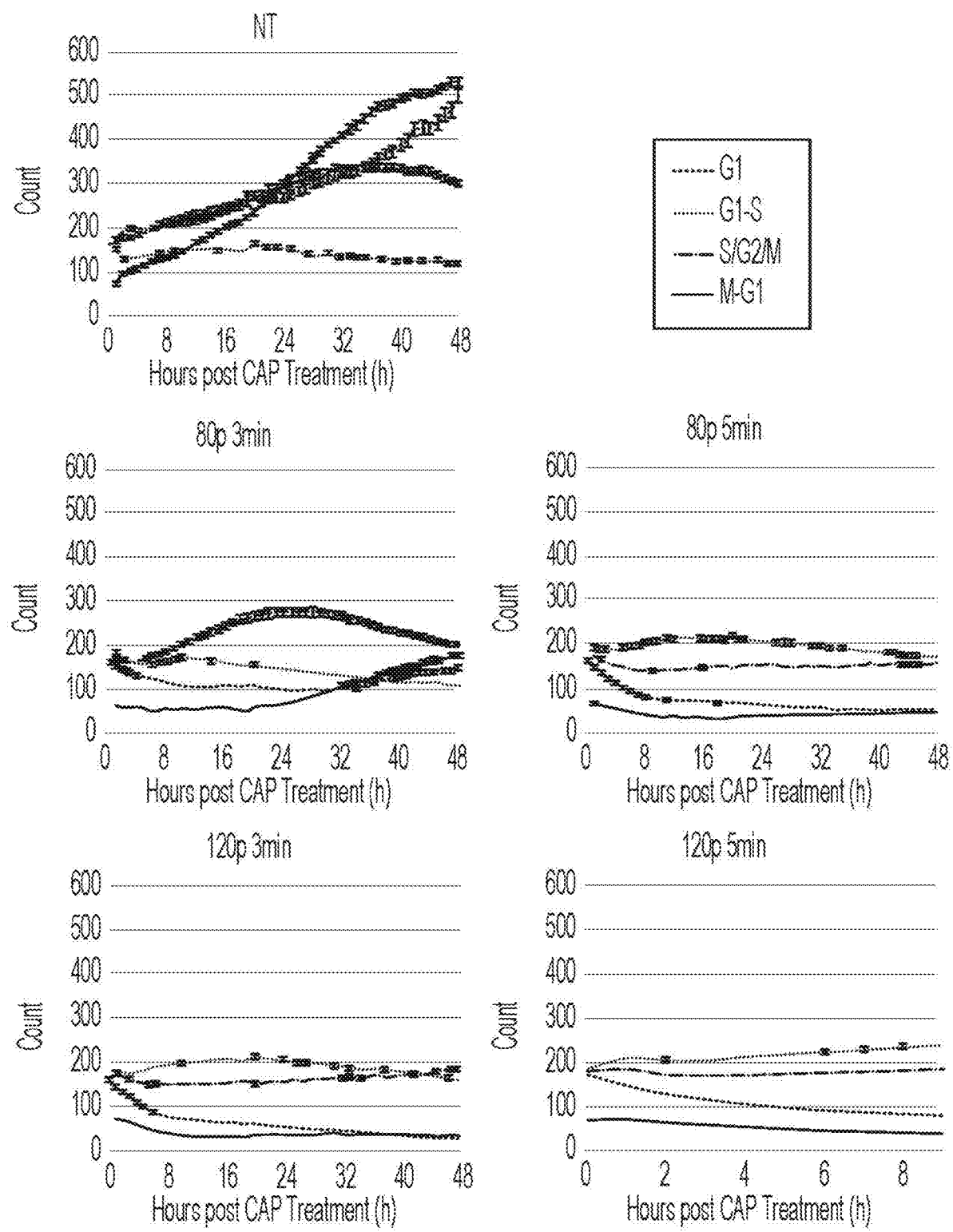
FIG. 13 shows quantification of MDA-MB-231 (TNBC) cells in G1, G1-S, S/G2/M, and M-G1 phases over 72 hours after CAP treatment. A-E) Cells were untreated or treated by CAP with various dosage.

For MCF-7 (ER$^+$PR$^+$HER2$^-$) cells treated with low doses of cold plasma treatment (80 p 3 min and 5 min, and 120 3 min, FIG. 11), during the first 8 hours post treatment the number of cells in G1 phase crashed down while the number of cells in G1-S transition phase and S/G2/M phase did not have significant changes. When treated with the highest dose of cold plasma (120 p 5 min), The number of cells in all phases decreased. the majority of cells died within 9 hours (FIG. 22) thus quantification was only plotted for 9 hours (FIG. 11).

Low doses of cold plasma treatment (80 p 3 min and 5 min, and 120 3 min) did not result in significant changes to the cell cycle of BT-474 (ER$^+$PR$^+$HER2$^+$), which is in correspondence with the caspase 3/7 activity (FIG. 6). With highest cold plasma dose at 120 p 5 min where apoptosis was observed (FIG. 6), the number of cells in G1 and S/G2/M drastically decreased whereas G1-S transition phase slightly increased suggesting that cell cycle did not progress from G1 to S/G2/M phases completely.

For MDA-MB-231 (TNBC), low doses of cold plasma (80 p 3 min and 5 min, 120 p 3 min) quickly decreased the number of cells at G1 phase within 8 hours but a limited number of cells progressed towards S/G2/M phases (yellow and green). High dose of cold plasma (120 p 5 min) induced apoptosis immediately thus the number of cells of all phases decreased.

Next Generation Sequencing (NGS) Whole Transcriptome Analysis of Histone Genes

Figure 14:
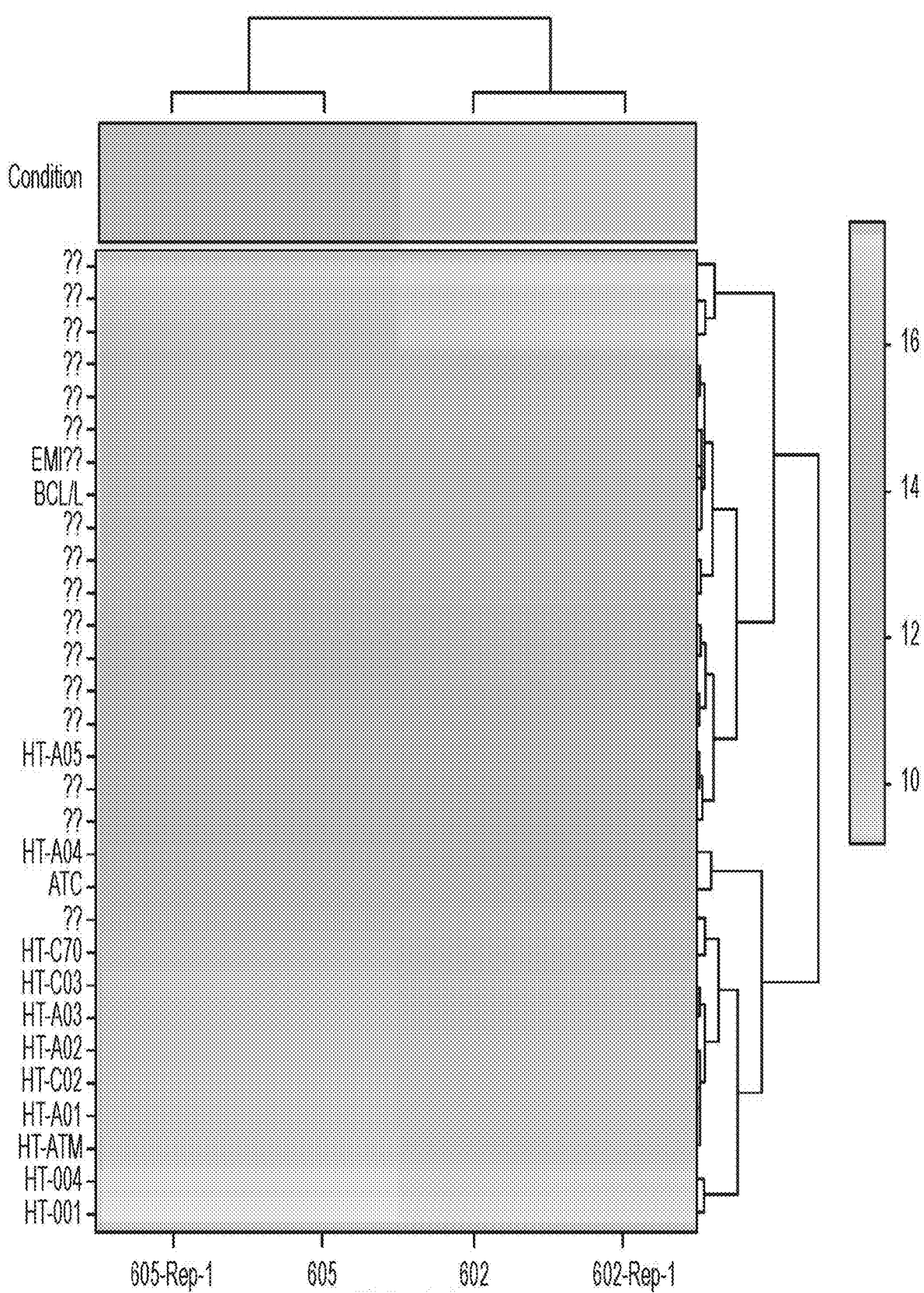
FIG. 14 is a heatmap of showing clustering of top 30 differentially expressed genes between CAP treated MDA-MB-231 cells (602) and mock controls (605). Gene expression levels are displayed on a log(absolute values) scale. Histone genes are very prominently displayed in the heatmap.
Figure 15:
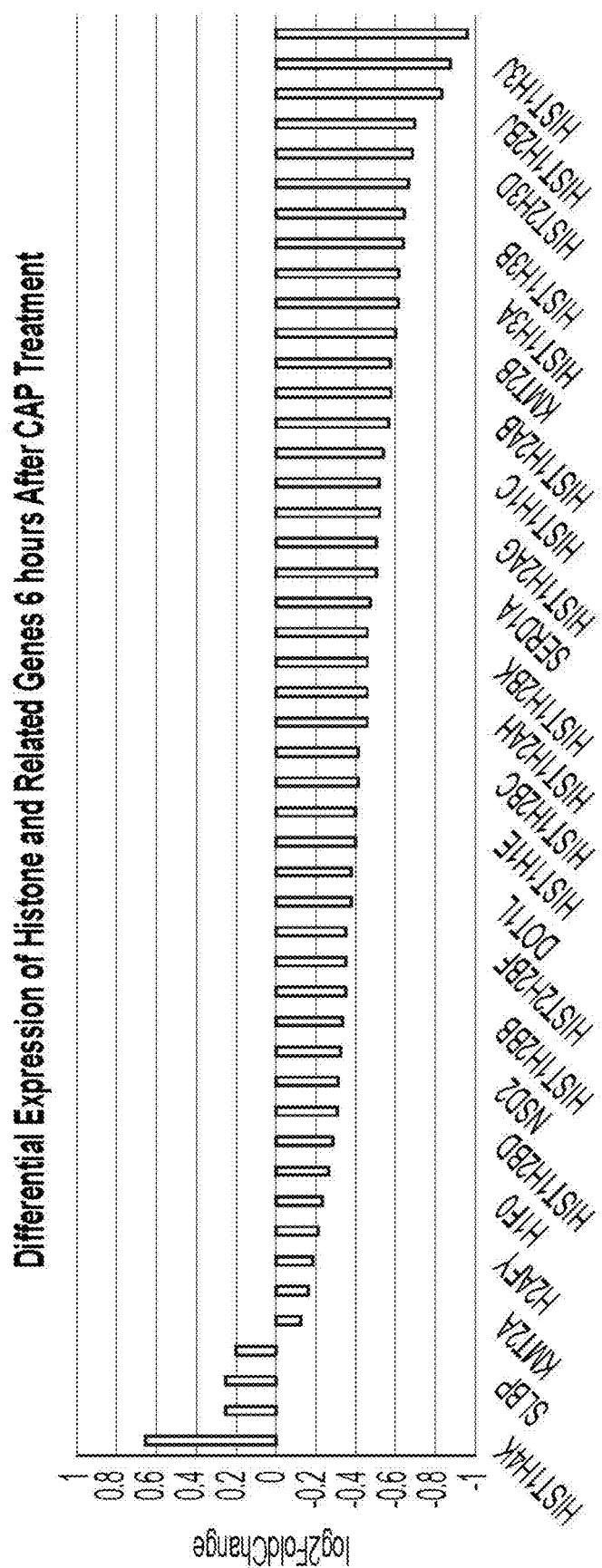
FIG. 15 is a bar graph showing the Next generation sequencing (NGS) whole transcriptome analysis in fold change (log 2 scale) of histone and histone related gene after 6 hours CAP treatment. MDA-MB-231 cells were CAP treated at 120 p for 5 mins and incubated for 6 hours. Ribosomal RNA was depleted from the total RNA and RNA sequencing library was prepped. Next generation sequencing (NGS) whole transcriptome sequencing were performed with illumina HiSeq 2×150 bp sequencing and downstream analyses with RNA-Seq data were performed by using DESeq2 and functional enrichment analysis using WebGestalt. Most of the histone and histone related genes were significantly down regulated after CAP treatment.

RNA sequencing technology has gained prominence for high throughput transcriptome analysis in recent years (Wang, Z., Gerstein, M. & Snyder, M. RNA-Seq: a revolutionary tool for transcriptomics. Nat Rev Genet 10, 57-63, doi:10.1038/nrg2484 (2009)), many breast cancer RNA transcriptomics studies have prognostic markers as well as novel therapeutic targets (Eswaran, J. et al. Transcriptomic landscape of breast cancers through mRNA sequencing. Sci Rep 2, 264, doi:10.1038/srep00264 (2012), Horvath, A. et al. Novel insights into breast cancer genetic variance through RNA sequencing. Sci Rep 3, 2256, doi:10.1038/srep02256 (2013) and Chen, F. et al. RNA-seq analysis identified hormone-related genes associated with prognosis of triple negative breast cancer. J Biomed Res 34, 129-138, doi: 10.7555/JBR.34.20190111 (2020)). However, breast cancer RNA transcriptomics after CAP treatment has not been investigated. In order to reveal the potential genes and mechanisms involved in CAP induced cell death, we used a NGS approach with Illumina HiSeq as a means of examining and comparing the transcriptomes of cold plasma-treated breast cancer cell lines. Here TNBC cell line MDA-MB-231 cells were treated at 120 p for 5 min and cells were harvested 6 hours post treatment for total RNA isolation followed by DNA clean up, RNA-Seq-Library Preparation with rRNA depletion and HiSeq Sequencing and data analysis as described in Materials and Methods section. A total of 45,037,559 and 37,683,510 reads, for mock control and treated sample cells respectively, were sequenced. Gene expression of mock (control) MDA-MB-231 cells was used as a baseline for up- or down-regulation of expression in cold plasma-treated cells. Poor quality read using Trimmomatic v.0.36 and map Homo sapiens reference genome available on ENSEMBL using the STAR aligner v.2.5.2b. A total of 97.8% and 98.2% reads were mapped for mock and treated sample cells respectively. Only unique reads that fell within exon regions were counted. Using DESeq2 differential expression analysis between the groups of samples was performed and genes with adjusted p-values <0.05 and absolute log 2 fold changes>1 were called as differentially expressed genes for each comparison. From a total of 25,671 mRNA genes, 75 were differentially expressed (44 up-regulated and 35 down-regulated) between the mock control and cold plasma treated samples. Because only a small number of genes were differentially expressed, we next sought manual method to categorize the genes based on their levels of differential expression to determine if any new patterns emerged. Histone genes were very prominent among different class of genes such as Zinc finger proteins, long non-coding RNAs and kinases (FIG. 14). The 24 histones and histone related genes were differentially expressed in the cold plasma-treated samples compared to mock (FIG. 15).

Figure 16A:
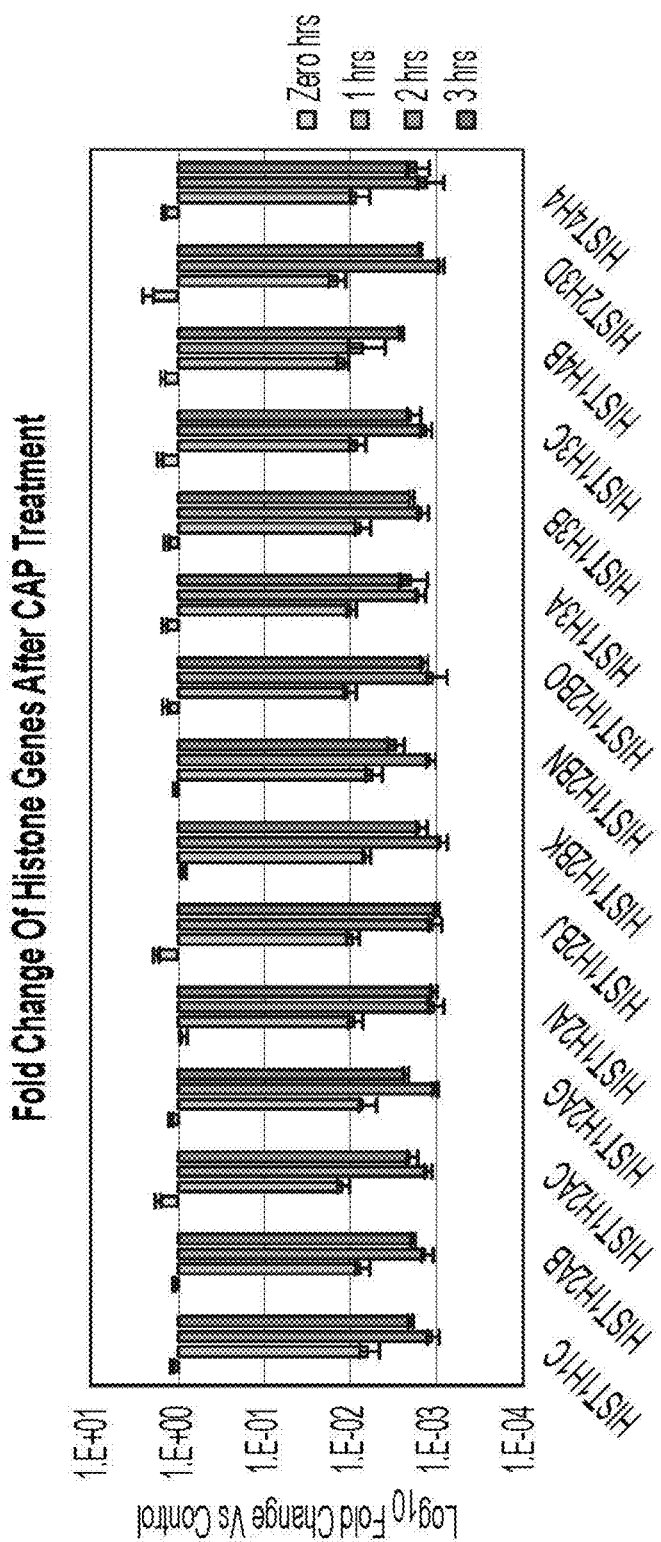
FIG. 16 shows histone RNA degradation after CAP treatment: (A) Bar graph showing the fold change of histone RNA after 0 hrs, 1 hrs, 2 hrs and 3 hrs post CAP treatment compared to the mock control samples of MDA-MB-231 cells. (B) Statistical analysis was performed using the repeated measures ANOVAs were used followed by post-hoc comparisons using Student t test with Bonferroni corrections as appropriate. *P<0.005.
Figure 16B:
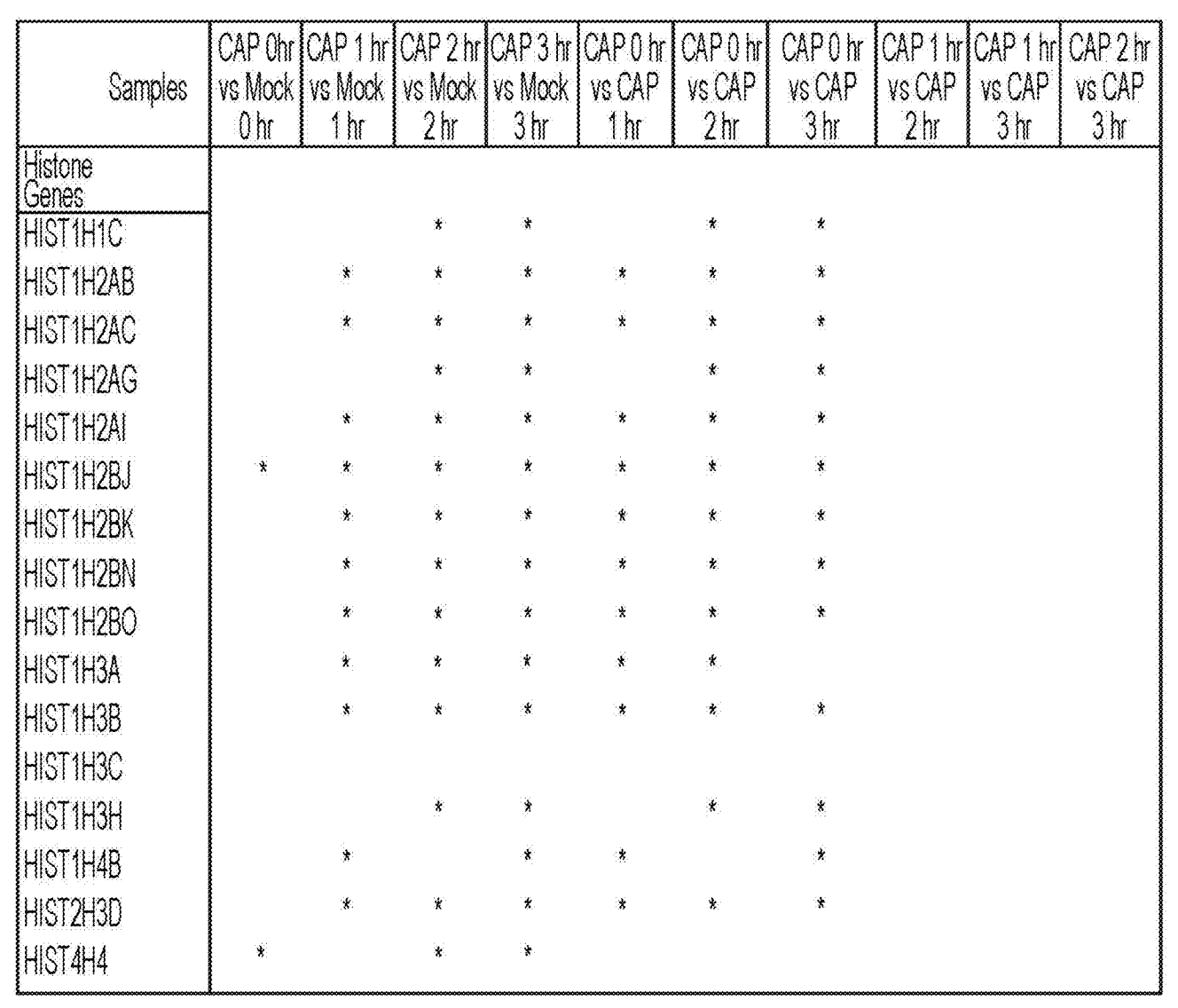
Figure 17:
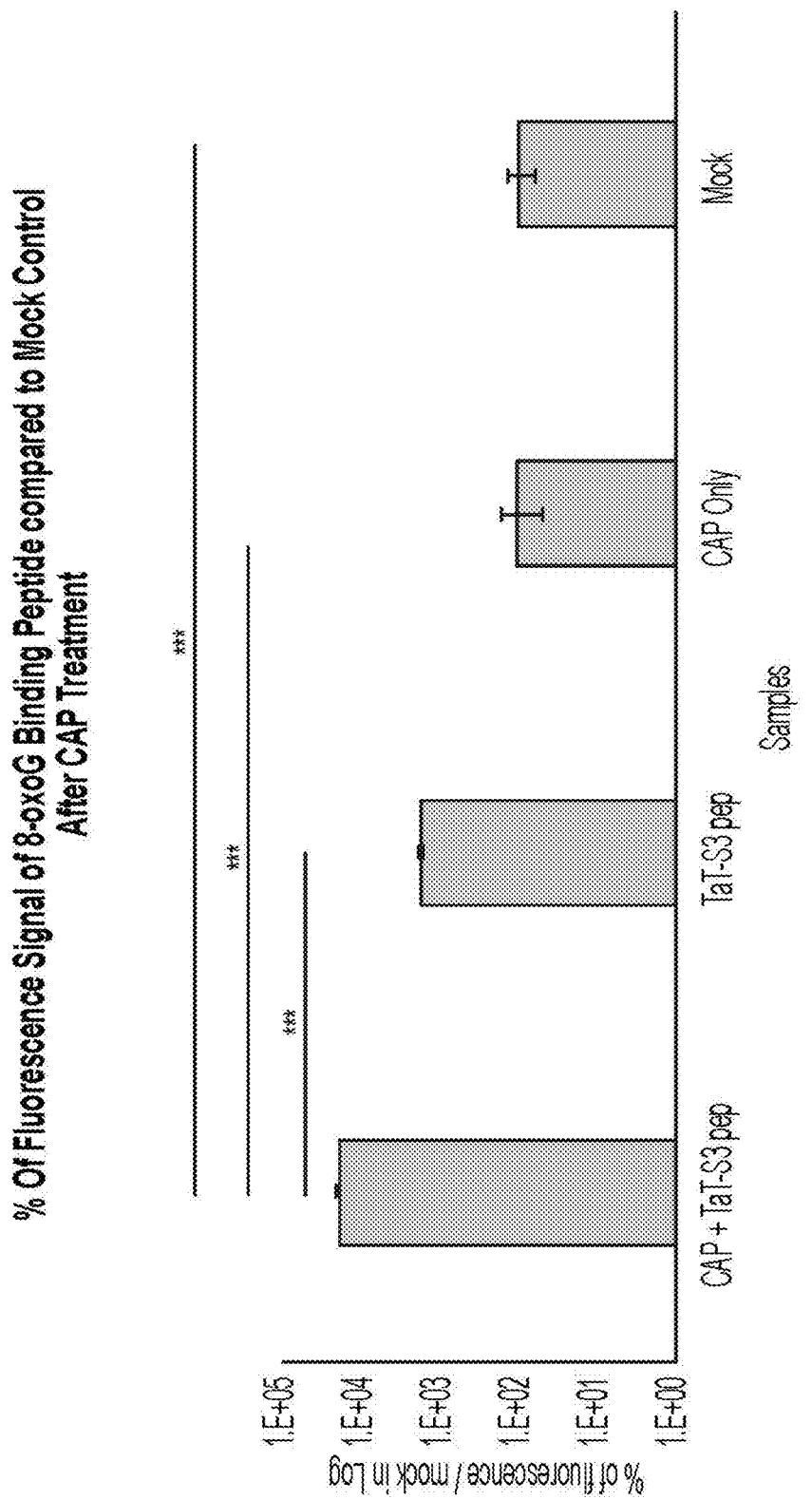
FIG. 17 is a bar graph showing the fluorescence intensity of RNA oxidation probed in situ with fluorescent tagged 8-oxoG binding peptide probe on CAP treated or untreated live MDA-MB-231 cells. MDA-MB-231 cells were CAP treated at 120 p 5 mins and after an hour of incubation fluorescent tagged 8-oxoG binding peptide probe were allowed to bind overnight and the following day media were removed and replaced with PBS. Fluorescence intensity of the in situ 8-oxoG bound probes were read at 485 nm wavelength. Relative fluorescence intensity is reported as percent compared to mock controls. At least a hundred-fold higher 8-oxoG binding is found in CAP treated-Tat-S3 peptide probed MDA-MD-231 cells compared to Tat-S3 peptide treated alone. The average SEM of the ratios is plotted. Statistical analysis was performed using the repeated measures ANOVAs were used followed by post-hoc comparisons using Student t test with Bonferroni corrections as appropriate. ***$P<0.001$.

To further analyze the differential expression of histone genes in cold plasma-treated and mock groups, we choose 15 histone genes and compared their mRNA levels at 0, 1, 2 and 3 hours after cold plasma treatment in MDA-MB-231 cells using quantitative RT-PCR (qRT-PCR). These four-time points were arbitrarily chosen to assess the initial expressions of histone genes after cold plasma treatment. Three replicates from cell culture experiments were prepared on three separate days that were distinct from those used for NGS. FIG. 16A shows the mRNA levels of the selected genes as determined by qRT-PCR. The qRT-PCR showed the downregulation of the histone mRNA initiated as soon as the first hour of incubation after cold plasma treatment (FIG. 16A). The down regulation of the 15 histone mRNAs were several folds lower than the fold-changes observed by the NGS. The down-regulated genes HIST1H1C (ANOVA for 0, 1, 2 and 3-hrs groups: $F[6, 14]=442.76$, $P<0.003E-9$), HIST1H2AB ($F[6, 14]=485.59$, $P<0.005E-9$), HIST1H2AC ($F[6, 14]=425.41, P<0.005E-9$), HIST1H2AG ($F[6, 14]=466.46, P<0.002E-9$), HIST1H2AI ($F[6, 14]=401.45, P<0.007E-9$), HIST1H2BJ ($F[6, 14]=530.21, P<0.001E-9$), HIST1H2BK ($F[6, 14]=1075.2, P<0.008E-9$), HIST1H2BN ($F[6, 14]=377.5, P<0.001E-8$), HIST1H2BO ($F[6, 14]=364.21, P<0.001E-9$), HIST1H3A ($F[6, 14]=210.26, P<0.006E-7$), HIST1H3B ($F[6, 14]=333.91, P<0.002E-8$), HIST1H3C ($F[6, 14]=382.34, P<0.001E-8$), HIST1H3H ($F[6, 14]=345.52, P<0.002E-8$), HIST1H4B ($F[6, 14]=345.52, P<0.002E-8$), HIST2H3D ($F[6, 14]=117.6, P<0.003E-6$), HIST4H4 ($F[6, 14]=434.58, P<0.0034E-9$). The significance of down regulation by statistical analyses at different time-points compared to mock controls has been shown in FIG. 16B. The only histone mRNA which did not show statistical significance compared to control is HIST1H3C, however the general trend was similar to other histone mRNAs. None have these mRNAs showed statistical significances between 1 hr to 3 hrs groups unlike zero hours group (p<0.01). Except for mRNAs HIST1H2BN, HIST1H2BK, HIST1H2AI all other histone mRNAs were generally up regulated at zero-hour incubation time point compared to controls, HIST4H4 (p<0.01) and HIST1H2BJ (p<0.01) showed significance. It was interesting that all histone mRNAs are highly down-regulation in the cold plasma treated groups after one-hour incubation, suggesting a distinct mechanism for the emergence of histone related cell death induced by cold plasma. Thus, qPCR validation of histone mRNA down regulation prompted us to further explore the mechanism of cold plasma induced cell death.

In Situ 8-oxoG Modification of RNA by Cold Plasma Treatment

Recent studies have shown that CAP generated reactive oxygen and nitrogen species (RONS) could induce 8-oxoguanine (8-oxoG) formation in nucleic acids (Kurita, H., Haruta, N., Uchihashi, Y., Seto, T. & Takashima, K. Strand breaks and chemical modification of intracellular DNA induced by cold atmospheric pressure plasma irradiation. PLoS One 15, e0232724, doi:10.1371/journal.pone.0232724 (2020)). To investigate the in situ 8-oxoG modification on RNA after cold plasma treatment, we modified and generated a previously designed (Gonzalez-Rivera, J. C. et al. RNA oxidation in chromatin modification and DNA-damage response following exposure to formaldehyde. Sci Rep 10, 16545, doi:10.1038/s41598-020-73376-7 (2020)) human ribosomal protein S3 (hRpS3) peptide probe (TaT-S3-peptide) that binds tightly to 8-oxoG sites on RNA as described in the method section. The fluorescence signals were compared between CAP treated- and untreated-cells probed or not probed with TaT-S3-peptide (ANOVA for CAP-TaT-S3, mock-TaT-S3, CAP, and mock groups: F[3, 40]=587.78, P<4.3E-33). The average fluorescence signal in CAP-TaT-S3 group and mock-TaT-S3 group were 20410% and 1738% respectively compared to unprobed CAP or mock groups (t test P<1.96E-11). The CAP-TaT-S3 group was 1174% higher than mock-TaT-S3 group (t test P<1.36E-11), even though there were only ~50% of the cold plasma treated cells in the wells compared to mock-TaT-S3 control group because of cell death induced by cold plasma. The results demonstrate that there were high incidents of 8-oxoG formation in the nuclei acids of cold plasma-treated TNBC cells and the down regulation observed in RNASeq data and qRT-PCR analysis would be due to the 8-oxoG modification of histone mRNAs.

Histone RNA are 8-oxoG Modified after Cold Plasma Treatment

Figure 18A:
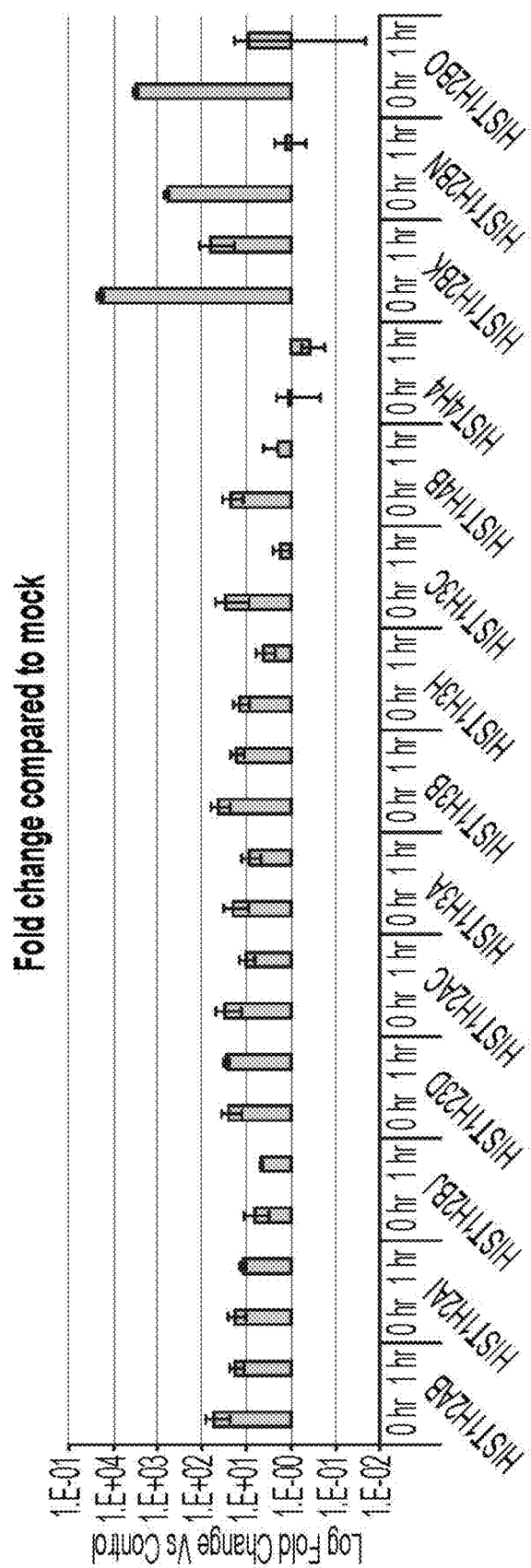
FIG. 18 shows a pull-down of 8-oxoG Histone RNA: (A) Bar graph showing the fold change of immunoprecipitated 8-oxoG histone RNA after 0 hrs and 1 hrs post CAP treatment compared to the immunoprecipitated 8-oxoG mock control samples of MDA-MB-231 cells. (B) Statistical analysis was performed using the repeated measures ANOVAs followed by post-hoc comparisons using Student t test with Bonferroni corrections as appropriate. *$P<0.005$.
Figure 19A:
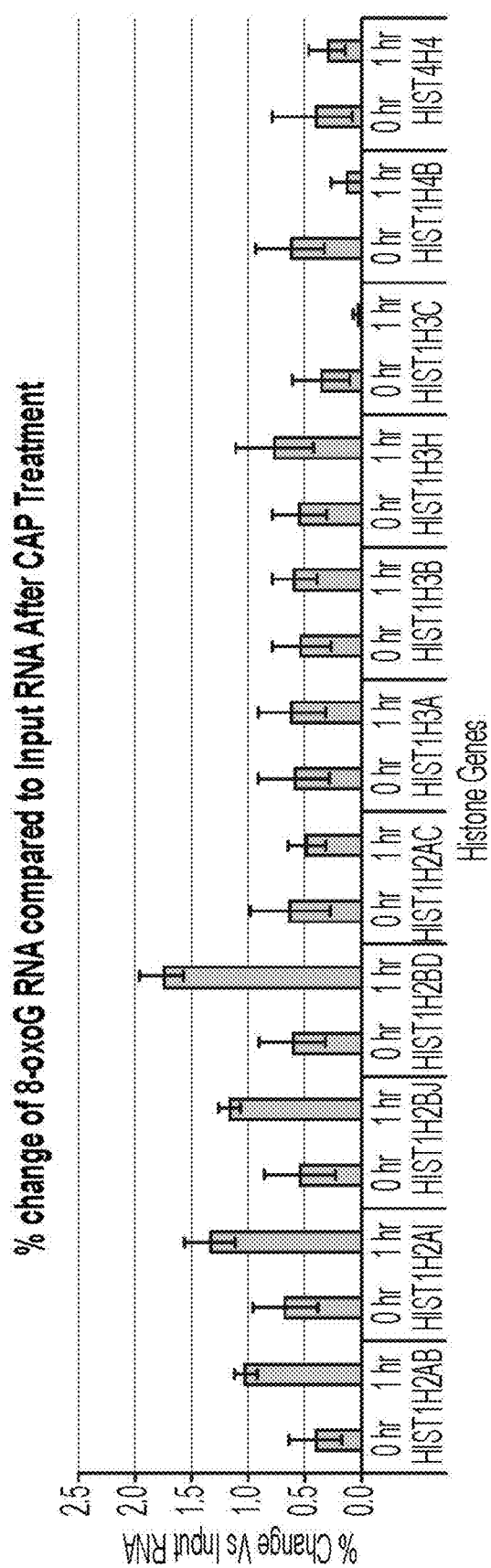
FIG. 19 is a bar graph showing the percentage change of 8-oxoG modification in the histone genes at zero hour and one hour incubation after CAP treated in MDA-MB-231 cells between CAP-8-oxoG immunoprecipitated group and input group.
Figure 19B:
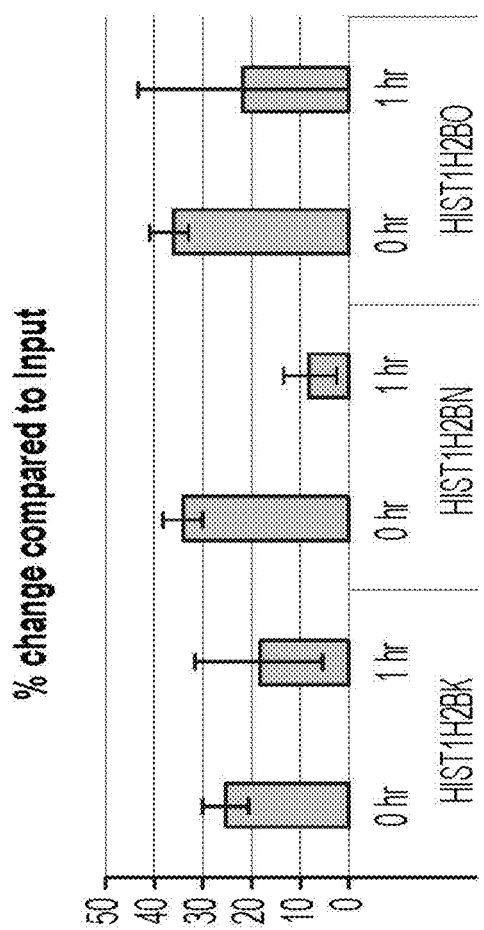

After we found out that 8-oxoG modification of nucleic acids were formed at high rate, it was prudent to investigate the 8-oxoG formation on histone RNA after CAP induction. One portion of total RNA from Mock Zero (MZ), one hour (M1), CAP Zero (CP0) and one hour (CP1) groups were used as inputs ($MZ_{IN}$, $M1_{IN}$, $CP0_{IN}$ and $CP1_{IN}$ respectively) and second portion of the total RNA was used to isolate 8-oxoG-containing transcripts via immunoprecipitation with an anti-8-oxoG antibody ($MZ_{IP}$, $M1_{IP}$, $CP0_{IP}$ and $CP1_{IP}$ respectively). These samples were used for first strand synthesis and qRT-PCR analysis of 16 histone genes (FIG. 18A). $CP0_{IP}$ and $CP1_{IP}$ group samples had significantly higher quantities of all the 16 histone genes compared to the $MZ_{IP}$ and $M1_{IP}$ groups. We performed Student's t tests with Bonferroni corrections as appropriate to find the significance among groups (FIG. 18B). There were significant (P<0.01) mRNA amplification difference between groups $CP0_{IP}$ Vs $MZ_{IP}$, $CP1_{IP}$ Vs $M1_{IP}$, $CP0_{IP}$ Vs $MZ_{IN}$, $CP1_{IP}$ Vs $M1_{IN}$ and $CP0_{IP}$ Vs $CP1_{IP}$ among all the histone genes analysed by qRT-PCR except the HIST1H3C between $CP1_{IP}$ Vs $M1_{IP}$ (P<0.014), HIST4H4 between $CP0_{IP}$ Vs $MZ_{IN}$ (P<0.012), HIST1H2BK, HIST1H2BN, HIST1H2BO between $CP1_{IP}$ Vs $M1_{IN}$ (P<0.065; 0.08; 0.09 respectively) but were significant between $CP0_{IP}$ Vs $CP1_{IP}$ (P<0.0009; 0.003; 0.005 respectively) unlike other histones, however the trend for these genes were similar to others that were significant. We quantified the percentage of 8-oxoG modification on histone RNA in $CP0_{IP}$ and $CP1_{IP}$ compared to the $CP0_{IN}$ and $CP1_{IN}$ groups (FIG. 19). The 8-oxoG modification events were significantly higher in $CP0_{IP}$ and $CP1_{IP}$ compared to $CP0_{IN}$ and $CP1_{IN}$ groups (P<0.001) in all the histone genes analyzed. Taken together, our data provides evidence of 8-oxoG oxidative modification in these 16 histone mRNAs in cold plasma-treated TNBC cells. Importantly, the negative fold change in histone mRNA (FIG. 16) is due to the 8-oxoG modification and degradation of histone mRNA rather than regulation at the transcription level.

DNA Damage Induced by Cold Plasma Comes after RNA Oxidation

Figure 20:
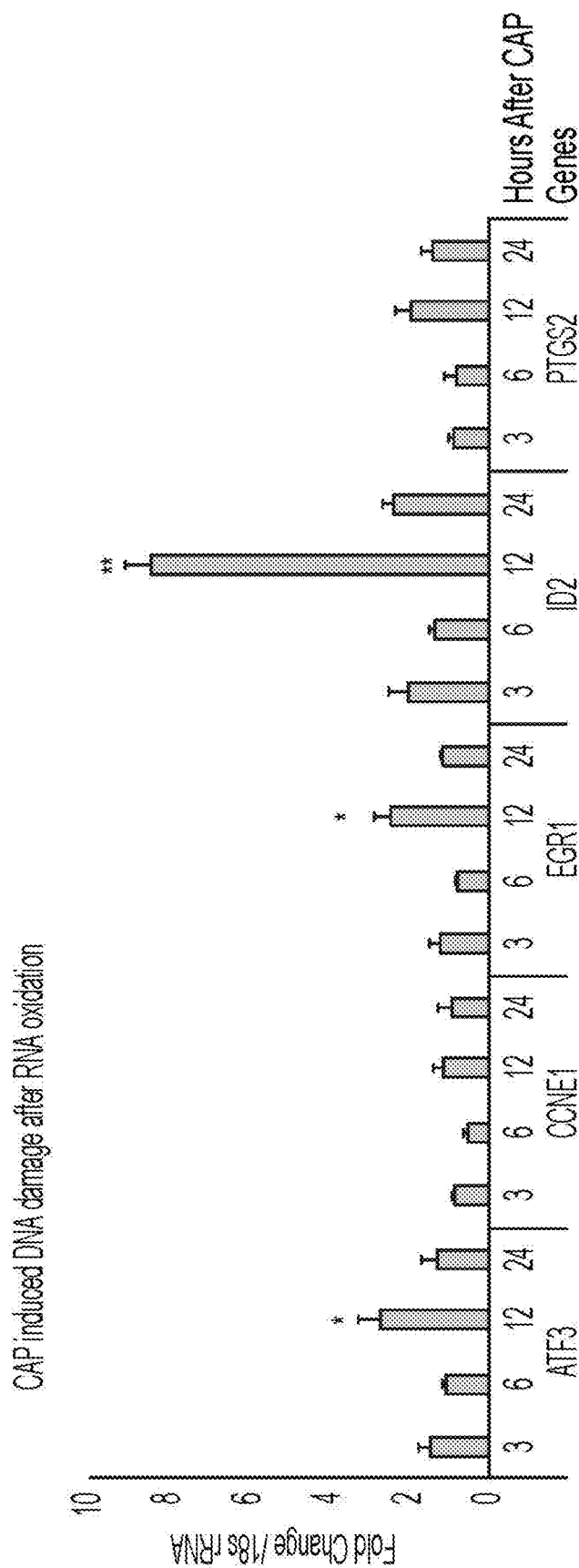
FIG. 20 Is a bar graph showing the fold changes of DNA damage response genes ATF3, CCNE1, EGR1, ID2 and PTGS2 genes compared to mock controls in MDA-MB-231 cells post CAP treatment at different incubation time points (3, 6, 12, & 24 hours). Statistical analysis was performed using Student t test. *$P<0.005$; **$P<0.001$.
Figure 21:
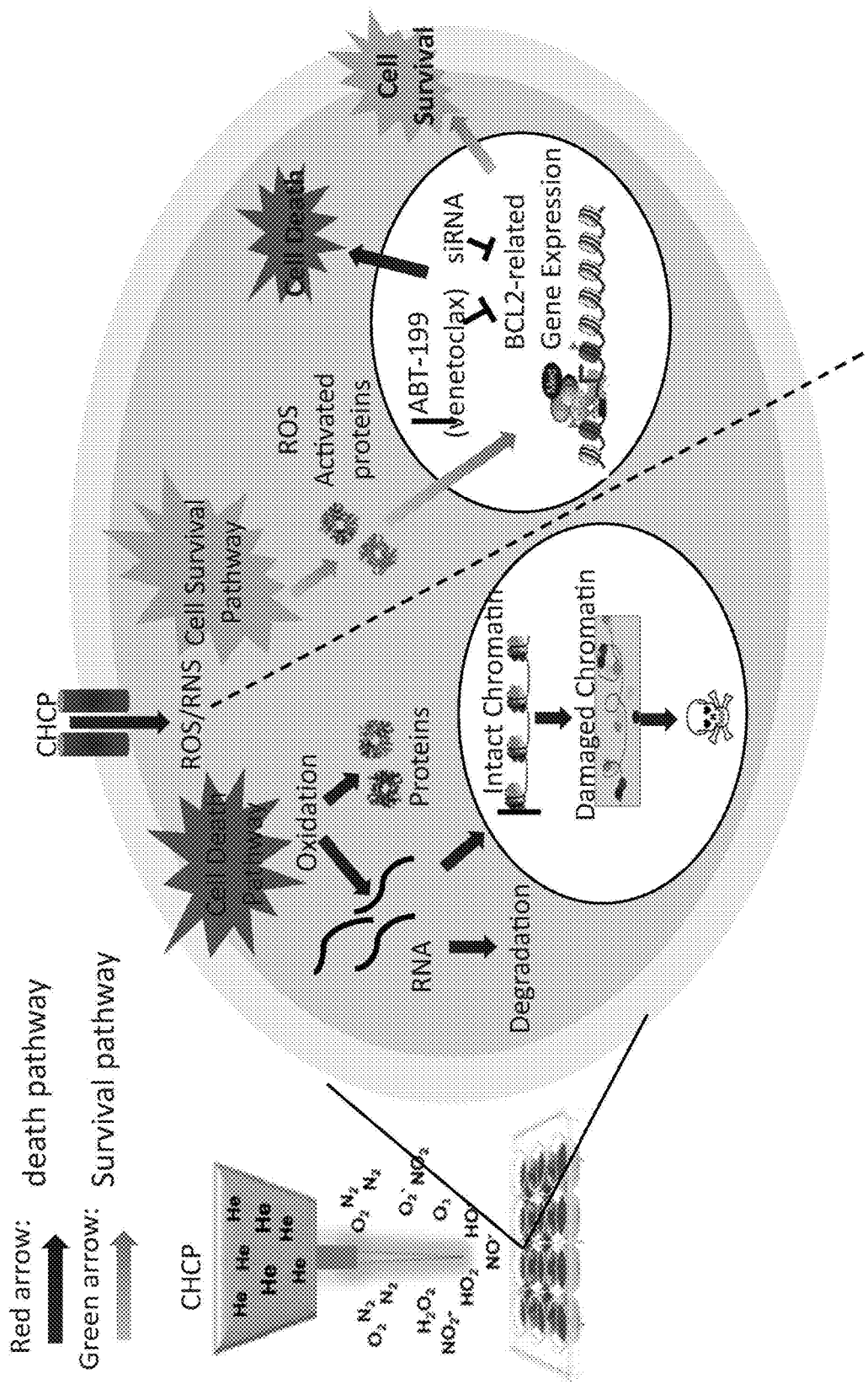
FIG. 21 is a diagram illustrating the mechanism of cold plasma induced apoptosis in accordance with the present invention.

To understand the mechanism of primary contributor to cell death induced by CAP treatment, TNBC cells were treated at conditions mention before and incubated for 3, 6, 12 and 24 hours followed by total RNA isolation and first strand synthesis. The expression of DNA damage response genes, Activating transcription factor 3 (ATF3) (Yan, C., Lu, D., Hai, T. & Boyd, D. D. Activating transcription factor 3, a stress sensor, activates p53 by blocking its ubiquitination. EMBO J 24, 2425-2435, doi:10.1038/sj.emboj.7600712 (2005)), Cyclin E1 (CCNE1) (Guerrero Llobet, S. et al. Cyclin E expression is associated with high levels of replication stress in triple-negative breast cancer. NPJ Breast Cancer 6, 40, doi:10.1038/s41523-020-00181-w (2020)), Early Growth Response 1 (EGR1) (Krones-Herzig, A. et al. Early growth response 1 acts as a tumor suppressor in vivo and in vitro via regulation of p53. Cancer Res 65, 5133-5143, doi:10.1158/0008-5472.CAN-04-3742 (2005)), Inhibitor Of DNA Binding 2 (ID2) and Prostaglandin-Endoperoxide Synthase 2 (PTGS2) genes compared to mock groups were quantified by qRT-PCR (FIG. 20). These are early responders of DNA damage and we found significant up-regulation of ATF3, EGR1 and ID2 genes transcripts (P<0.05) by more than two-fold increase only after 12 hours of incubation. CCNE1 and PTGS2 showed no significant up-regulation at any of the time points compared to mock controls. These results show that DNA damage is not the primary cause of cold plasma induced cell death in TNBC cells.

Discussion

In the past decades, studies on a variety of tumor cell types have been published using different CAP devices. CCPCS has been previously demonstrated as a promising anti-cancer treatment for several cancers including TNBC (Rowe, W. et al. The Canady Helios Cold Plasma Scalpel Significantly Decreases Viability in Malignant Solid Tumor Cells in a Dose-Dependent Manner. Plasma 1, 177-188, doi:10.3390/plasma1010016 (2018) and Cheng, X. et al. Treatment of Triple-Negative Breast Cancer Cells with the Canady Cold Plasma Conversion System: Preliminary Results. Plasma 1, 218-228, doi:10.3390/plasma1010019 (2018)). Molecular features and corresponding tumor subtypes of each breast tumor cell lines are feasible as models for tumors of the same subtype (Dai, X., Cheng, H., Bai, Z. & Li, J. Breast Cancer Cell Line Classification and Its Relevance with Breast Tumor Subtyping. J Cancer 8, 3131-3141, doi:10.7150/jca.18457 (2017)). We are the first to analyze dose-dependent apoptotic effect of CAP on breast cancer cell lines based on molecular subtypes using cold plasma via monitoring Ki-67 expression, apoptosis progression, and cell cycle. Ki-67 expression is an independent prognostic parameter according to breast cancer molecular subtypes in breast cancer patients (Soliman, N. A. & Yussif, S. M. Ki-67 as a prognostic marker according to breast cancer molecular subtype. Cancer Biol Med 13, 496-504, doi:10.20892/j.issn.2095-3941.2016.0066 (2016)). Soliman et al. reported that patients with Ki-67 expression higher than 15% exhibited higher incidence of metastasis and recurrence (p=0.000) (Soliman, N. A. & Yussif, S. M. Ki-67 as a prognostic marker according to breast cancer molecular subtype. Cancer Biol Med 13, 496-504, doi:10.20892/j.issn.2095-3941.2016.0066 (2016)) and Ki67 decrease significantly improved disease-free survival and overall survival. At molecular level, expression, localization and post translational modification of Ki-67 are regulated by the cell cycle (Endl, E. & Gerdes, J. Posttranslational Modifications of the Ki-67 Protein Coincide With Two Major Checkpoints During Mitosis. Journal of Cellular Physiology 182, 371-3880 (2000)), during early G1 phase, the Ki-67 antigen is located in the nucleoplasma unlike nucleolus location in S and G2 phase[74] and is regulated differently in non-cancerous and cancerous cells (Chierico, L. et al. The role of the two splice variants and extranuclear pathway on Ki-67 regulation in non-cancer and cancer cells. PLoS One 12, e0171815 (2017)), providing an insight for the mechanism of CAP selectivity towards cancerous cells. Our data of Ki-67 expression for the 4 breast cancer subtypes indicates the down-regulation of Ki-67 by cold plasma with slightly different dosages.

Molecular pathways of metastasis across 3 breast carcinoma subtypes including $HR^+$, TNBC, and $HER2^+$ have been studied using a proteomic approach (Negro, G. et al. Molecular heterogeneity in breast carcinoma cells with increased invasive capacities. Radiol Oncol 54, 103-118 (2020)), suggest that $HR^+$ breast cancer shared similarities with TNBC cells, whereas $HER2^+$ cells specifically changed their molecular phenotype resulting in highest metastatic potential.

Apoptosis induction by cold plasma treatment were dose-dependent, which was quantitatively and visually assayed by flow cytometry and by IncuCyte for each molecular sub-types of breast cancer cell line. Apoptosis was seen earlier in the cells treated with higher cold plasma treatment power and time. Previously, Park et al. reported that MDA-MB-231 (TN) underwent a higher rate of apoptosis and a decreased proliferation rate upon cold plasma treatment than MCF-7 ($ER^+PR^+HER2^-$) cells (Park, S. B. et al. Differential Epigenetic Effects of Atmospheric Cold Plasma on MCF-7 and MDA-MB-231 Breast Cancer Cells. PLoS One 10, e0129931 (2015)), which is in agreement with our finding. In addition, $HER2^+$cell lines showed a more sensitive response while BT-474 ($ER^+PR^+HER2^+$) was the most resistant to cold plasma treatment. Temporal progression of cell cycle data demonstrates that the number of cells in G1 phases decreased quickly within the first 8 hours after cold plasma treatment, but the increase of G1-S transition phase or S/G2/M phases during this period was much smaller if present, suggesting the transition from G1 to S/G2/M phases were disrupted by cold plasma.

Cold atmospheric plasma and its anti-cancer effects have been reported repeatedly over the last two decades. However, the mechanism of CAP induce cell death in malignant cells rather than normal cells was not yet established. Several studies have reported the phosphorylation of H2AX with CAP treatment on different cancer types thus concluded that plasma-generated ROS induce DNA damage (Chang, J. W. et al. Non-thermal atmospheric pressure plasma induces apoptosis in oral cavity squamous cell carcinoma: Involvement of DNA-damage-triggering sub-G(1) arrest via the ATM/p53 pathway. Arch Biochem Biophys 545, 133-140 (2014), Kaushik, N. et al. Responses of solid tumor cells in DMEM to reactive oxygen species generated by non-thermal plasma and chemically induced ROS systems. Sci Rep 5, 8587 (2015), Judee, F. et al. Short and long time effects of low temperature Plasma Activated Media on 3D multi-cellular tumor spheroids. Sci Rep 6, 21421 (2016) and Sagwal, S. K., Pasqual-Melo, G., Bodnar, Y., Gandhirajan, R. K. & Bekeschus, S. Combination of chemotherapy and physical plasma elicits melanoma cell death via upregulation of SLC22A16. Cell Death Dis 9, 1179 (2018)). Recently, Bekeschus et al (Bekeschus, S. et al. Elevated H2AX Phosphorylation Observed with kINPen Plasma Treatment Is Not Caused by ROS-Mediated DNA Damage but Is the Consequence of Apoptosis. Oxid Med Cell Longev 2019, 8535163, doi:10.1155/2019/8535163 (2019)) argued that DNA damage was a consequence rather than cause for CAP-induced cell death. Our data is in agreement with this finding by demonstrating oxidation enrichment of histone RNA transcripts in CAP treated cells compared to control groups. Although RNA oxidation altered expression levels of many transcripts, this was particularly pronounced on transcripts involved in chromatin modification and DNA-damage response. Our data showed that the transcriptional activation of DNA damage early response genes ATF3 (Zhao, J., Li, X., Guo, M., Yu, J. & Yan, C. The common stress responsive transcription factor ATF3 binds genomic sites enriched with p300 and H3K27ac for transcriptional regulation. BMC Genomics 17, 335 (2016)), EGR1 (Stuart, J. R., Kawai, H., Tsai, K. K., Chuang, E. Y. & Yuan, Z. M. c-Abl regulates early growth response protein (EGR1) in response to oxidative stress. Oncogene 24, 8085-8092 (2005)), and ID2 (Fan, Y. et al. ID2 protects retinal pigment epithelium cells from oxidative damage through p-ERK1/2/ID2/NRF2. Arch Biochem Biophys 650, 1-13 (2018)) occurred only at 12 hours after CAP treatment, a late response in DNA damage response genes. These observed alterations were considered as an indicative of cellular responses rather than consequences of apoptosis and necrosis.

Moreover, the cell cycle analysis after cold plasma treatment revealed a significant decrease in the number of cells at G1 with higher number of cells that were in S/G2/M phase with strong cold plasma dosage when apoptosis activity was induced, connotatively demonstrating that the machinery and components required for the S phase of the cell cycle to proceed were impaired or unavailable (Nelson, D. M. et al. Coupling of DNA synthesis and histone synthesis in S phase independent of cyclin/cdk2 activity. Mol Cell Biol 22, 7459-7472 (2002)). The ability of cold plasma treatment to induce specific 8-oxoG modification in the RNA molecules and to subsequently compromise the stability of these modified histone transcripts and their associated pathways represents a potentially novel mechanism for the detrimental and apoptotic effects of cold plasma treatment. Growing evidence suggests that RNA oxidation might be involved in the chromatin destabilization and cell death (Li, Z. et al. Recent Advances: Molecular Mechanism of RNA Oxidation and Its Role in Various Diseases. Front Mol Biosci 7, 184 (2020) and Liu, T. et al. The mechanism of RNA oxidation involved in the development of heart failure. Free Radic Res 53, 910-921 (2019)). Primarily studies have focused on RNA oxidation and oxidative stress and degeneration to neurological disorders (Liguori, I. et al. Oxidative stress, aging, and diseases. Clin Interv Aging 13, 757-772 (2018) and Nunomura, A., Lee, H. G., Zhu, X. & Perry, G. Consequences of RNA oxidation on protein synthesis rate and fidelity: implications for the pathophysiology of neuropsychiatric disorders. Biochem Soc Trans 45, 1053-1066 (2017)), we are first to report that RNA oxidation is the primary cause of cold plasma induced cell death in cancer cells. Studies have shown that 8-oxoG could base pair with adenosine and hence mRNA oxidation can introduce amino acid point mutations (Simms, C. L., Hudson, B. H., Mosior, J. W., Rangwala, A. S. & Zaher, H. S. An active role for the ribosome in determining the fate of oxidized mRNA. Cell Rep 9, 1256-1264 (2014) and Tanaka, M., Chock, P. B. & Stadtman, E. R. Oxidized messenger RNA induces translation errors. *Proc Natl Acad Sci USA* 104, 66-71 (2007)) which leads to errors in translation and destabilization of the proteins. Literature have also argued the about 8-oxoG RNA oxidation and RNA stability (Boo, S. H. & Kim, Y. K. The emerging role of RNA modifications in the regulation of mRNA stability. Exp Mol Med 52, 400-408 (2020)). RNASeq data showed that histone mRNAs are predominantly differentially expressed (FIGS. 14 and 15) and the qRT-PCR quantification (FIGS. 16-19) suggest that 8-oxoG RNA modification of histone mRNA also leads to its degradation. Histones H2A and H2B are the key proteins in packaging of DNA into nucleosomes (Wyrick, J. J. & Parra, M. A. The role of histone H2A and H2B post-translational modifications in transcription: a genomic perspective. Biochim Biophys Acta 1789, 37-44 (2009)) and are replication-dependent and cell-cycle-regulated, increasing 15 to 35-fold in S phase during DNA replication (Harris, M. E. et al. Regulation of histone mRNA in the unperturbed cell cycle: evidence suggesting control at two posttranscriptional steps. Mol Cell Biol 11, 2416-2424, doi:10.1128/mcb.11.5.2416 (1991) and Heintz, N., Sive, H. L. & Roeder, R. G. Regulation of human histone gene expression: kinetics of accumulation and changes in the rate of synthesis and in the half-lives of individual histone mRNAs during the HeLa cell cycle. Mol Cell Biol 3, 539-550 (1983)). Given that histone gene transcription is tightly regulated during the S phase of cell cycle any alterations in histones by RNA degradation or unstable protein would be detrimental to chromatin stability and the cell survival. This phenomenon plays important role in the selectivity of cold plasma treatment on rapidly proliferating cancer cells rather than normal cells.

Furthermore, because of this aspect, breast cancer cell line subtypes required slightly different power or time settings to achieve 100% elimination. For example, rapidly proliferating TNBC MDA-MB-231 cells need shorter time cold plasma treatment compared to relatively slow-paced BT-474 ($ER^+PR^+HER2^+$) cells. Moreover, the expressions level of histone H2A and H2B variants have been shown to be varied among breast cancer cell line subtypes and were mediators of drug resistance (Braunstein, M. et al. Downregulation of histone H2A and H2B pathways is associated with anthracycline sensitivity in breast cancer. Breast Cancer Res 18, 16 (2016)), this variation in histone mRNA would also lead to different cold plasma power and treatment time for the setup. We believe cold plasma induced 8-oxoG RNA modification is not selective to any transcript, but the cell cycle dependent tight transcriptional regulation of histone RNA makes cold plasma treatment particular lethal to fast proliferating cancer cells rather than normal cells where other gene RNA transcripts could survive the cold plasma insults as they are not cell cycle dependant and could be replenished without delay. Furthermore, in normal dividing cell the half-life of histone mRNAs and their degradation are tightly regulated at the end of S-phase or when DNA replication is inhibited (Marzluff, W. F. & Koreski, K. P. Birth and Death of Histone mRNAs. Trends Genet 33, 745-759 (2017)). Given that cold plasma treatment induces 8-oxoG RNA modification and strand breaks in genomic DNA (Kurita, H., Haruta, N., Uchihashi, Y., Seto, T. & Takashima, K. Strand breaks and chemical modification of intracellular DNA induced by cold atmospheric pressure plasma irradiation. PLoS One 15, e0232724 (2020) and Bekeschus, S. et al. Elevated H2AX Phosphorylation Observed with kINPen Plasma Treatment Is Not Caused by ROS-Mediated DNA Damage but Is the Consequence of Apoptosis. Oxid Med Cell Longev 2019, U.S. Pat. No. 8,535,163 (2019)), ceasing of DNA replication could occur, making histone mRNA degradation even more pronounced.

The histone mRNA (HIST1H2AB (Zhong, B. L. et al. Identification of key genes involved in HER2-positive breast cancer. Eur Rev Med Pharmacol Sci 20, 664-672 (2016))) that we analysed in this study have been shown to be up-regulated in breast cancer tissue and in colorectal cancer (CRC) (Saleh, R. et al. Differential gene expression of tumor-infiltrating CD8(+) T cells in advanced versus early-stage colorectal cancer and identification of a gene signature of poor prognosis. J Immunother Cancer 8, doi:10.1136/jitc-2020-001294 (2020)) they were significantly enriched within the chromatin structure. HIST1H2AC, HIST1H2BF and HIST1H2BO are shown to be overexpressed in breast cancer cells contributing to the stability of the nucleosome structure for increased proliferation these cells (Parssinen, J. et al. Identification of differentially expressed genes after PPM1D silencing in breast cancer. Cancer Lett 259, 61-70 (2008)) and also mediate the up-regulation of BCL2 expression to stimulated cell proliferation (Su, C. H., Tzeng, T. Y., Cheng, C. & Hsu, M. T. An H2A histone isotype regulates estrogen receptor target genes by mediating enhancer-promoter-3'-UTR interactions in breast cancer cells. Nucleic Acids Res 42, 3073-3088 (2014)). Studies have also shown that chemoresistance in the human TNBC MDA-MB-231 cells were due to histone regulation specifically the up-regulation of HIST1H2BK (Han, J. et al. Chemoresistance in the Human Triple-Negative Breast Cancer Cell Line MDA-MB-231 Induced by Doxorubicin Gradient Is Associated with Epigenetic Alterations in Histone Deacetylase. J Oncol 2019, 1345026, doi:10.1155/2019/1345026 (2019)), HIST1H3C and HIST1H2AB (Chen, Y. Z. et al. PPAR signaling pathway may be an important predictor of breast cancer response to neoadjuvant chemotherapy. Cancer Chemother Pharmacol 70, 637-644 (2012)).

All the histone RNA that we analysed in this study have been shown to have variants that contributes to cancer development and progression (Monteiro, F. L. et al. Expression and functionality of histone H2A variants in cancer. Oncotarget 5, 3428-3443, doi:10.18632/oncotarget.2007 (2014)). High proliferation rate of cancer cells requires a coherent histone regulation, and any flaws would lead to chromatin instability and cell death. Taken together, our data provides evidence of oxidative modification in histone mRNA as the primary cause of cold plasma induced cell death.

Conclusion

In this study, we report that cold plasma as an effective treatment for all breast cancer subtypes, and the required dosage can be optimized based on receptor status. We are the first to show that cold plasma induced cell death is due to 8-oxoG RNA oxidation of histone RNA followed by degradation and chromatin destabilization at early S phase of cell cycle. This mechanism is the key differentiating factor in cold plasma therapy to selectively induce cell death in cancer cells without damaging normal tissue. Based on our study, conditions and standards could be improved to more precisely target this mechanism for advancing therapeutic inventions for breast and other cancers.

Methods and Materials

Cold Plasma Device

CAP was generated by the Canady Helios Cold Plasma™, which was reported in our previous publication (Cheng, X. et al. Treatment of Triple-Negative Breast Cancer Cells with the Canady Cold Plasma Conversion System: Preliminary Results. Plasma 1, 218-228 (2018)). CCPCS parameters were set as follows: helium flow rate at 3 L/min; power settings at 80 p (15.7 W), 100 p (22.3 W), and 120 p (28.7 W).

Cell Culture and Viability Assay

Cell culture. Human breast ductal carcinoma BT-474 and breast adenocarcinoma SK-BR-3 were purchased from ATCC (Manassas, VA, USA) and cultured according to provided protocol. Human adenocarcinoma cell lines MCF-7 and MDA-MB-231 were generously donated by Professor Kanaan's laboratory at Howard University. SK-BR-3 was cultured with McCoy's 5A and BT-474, MCF-7, and MDA-MB-231 were culture with RPMI 1640 medium supplemented with 10% fetal bovine serum (FBS) (Sigma-Aldrich, St. Louis, MO, USA) and 1% Pen Strep (Cat. #15140163, Thermo Fisher Scientific, Waltham, MA, USA). All cell lines were cultured in a 37° C. and 5% $CO_2$ humidified incubator (Thermo Fisher Scientific, Waltham, MA, USA). When reaching approximately 80% confluence, cells were seeded at a concentration of $10^5$ cells/well into 12-well plates (USA Scientific, Ocala, FL, USA) with 1 mL culture media per well for all assays.

Cell viability assay. Thiazolyl blue tetrazolium bromide (MTT) was purchased from Abcam (Cat. #ab146345) and viability assays were carried out after 48 hr CAP treatment according to the manufacturer's protocol. Briefly, cell culture media were replaced with MTT solution and incubated for 3 hours in a 37° C. and 5% $CO_2$ humidified incubator. MTT solution was then replaced with MTT solvent and read with a BioTek Synergy HTX (Winooski, VT, USA) microplate reader at 570 nm absorbance.

IncuCyte Live Cell Imaging for Caspase Activity and Cell Cycle

Caspase 3/7 activity. The IncuCyte® Caspase-3/7 Dyes for Apoptosis (Cat. #4440, IncuCyte) couple the activated caspase-3/7 recognition motif (DEVD (SEQ ID NO: 1)) to a DNA intercalating dye and are ideally suited to the mix-and-read, real-time quantification of cells undergoing caspase-3/7 mediated apoptosis. Addition of the IncuCyte® Caspase-3/7 Dyes to normal healthy cells is non-perturbing to cell growth and morphology. When added to tissue culture medium, the inert, non-fluorescent substrate crosses the cell membrane where it is cleaved by activated Caspase-3/7 resulting in the release of the DNA dye and fluorescent staining of the nuclear DNA.

Breast cancer cells were seeded in 12-well plates at a density of $10^5$ cells/well, treated or untreated with CAP, followed by staining with IncuCyte Caspase 3/7 dye. Then the cells were placed in IncuCyte and scanned with phase contrast and green channels at 10× magnification at an interval of 1 h for 3 days. After scanning, fluorescent object were quantified using the IncuCyte integrated analysis software with background subtraction.

Cell cycle tracking. The IncuCyte® Cell Cycle Green/Red Lentivirus Reagent (Cat. #4779, IncuCyte) is a fluorescent, single cassette indicator expressing both the GFP (green fluorescent protein) and mKate2 (red fluorescent protein) to distinguish between cells in the G1 and S/G2/M cell cycle phase without altering cell function. Stable cell populations for MCF-7, BT-474, and MDA-MB-231 cell lines were generated using puromycin selection. Stable cells were seeded in 12-well plates at a density of $10^5$ cells/well, treated or untreated with CAP and placed in IncuCyte for 3-day scanning. Cells were scanned every hour with phase contrast, green, and red channels at 10× magnification with Cell By Cell Module for MCF-7 and MDA-MBA-231 cells. For BT-474 cells, which tend to grow in clusters, Cell By Cell Module could not properly detect the boundaries between each cell, basic scanning and analysis was used.

Flow Cytometry

Apoptosis assays were carried out on all 4 breast cancer cell lines with FITC Annexin V (Cat. #556419, BD Biosciences) and PI (ThermoFisher, Cat. #P3566) by flow cytometry. Cells were seeded in 12-well plates and treated with CAP for various dosage. After incubated with desired periods of time, cell culture media was removed, and the cells were washed twice with PBS and detached with 250 μl of trypsin-EDTA (Sigma-Aldrich, Cat. #T4049). Please note that the culture media, the PBS for washing, as well as the trypsin-EDTA were all collected and spun down for apoptotic staining and analysis. Plotting of the data and analysis of the results were performed with FCS Express 7 (De Novo Software).

Confocal Microscopy

Immunofluorescent Staining and Imaging. Round cover glass (12 mm diameter, Fisher Scientific, Cat. #50-192-8952) were placed in 12-well plates and coated with fibronectin (Sigma-Aldrich, Cat. #F1141) and collagen I (ThermoFisher, Cat. #A1064401) for at least 1 hour prior to seeding cells. Seeding cells on cover slides in 12-well plates instead of chamber slides can produce consistent CAP treatment effect with various dosage since the well size and cell number remained the same as the viability assay by MTT and apoptosis assay by flow cytometry. After CAP treatment and desired periods of incubation time, cells were stained with Alexa Fluor 488 conjugated Ki-67 Rabbit mAb (Cell Signaling Technology, Cat. #11882) according to manufacturer's protocol. Briefly, cells were washed with phosphate buffered saline (PBS) and fixed with cold anhydrous methanol (pre-cooled in −80 C freezer) for 10 min at room temperature. After the methanol was aspirated, cells were washed twice with PBS and blocked in blocking buffer for 60 min. Then, Ki-67 and Isotype control (Cell Signaling Technology, Cat. #4340) antibodies were diluted with 1:200 dilution with antibody dilution buffer and 400 μl of which was added to designated wells. Cells were incubated overnight at 4 C refrigerator protected from light. Round cover slides with cells were washed twice before they were carefully moved onto 1"×3"×1 mm microscope slides. The cells were first covered with Antifade Mounting Reagent with DAPI (Vector Laboratories, Cat. #H-1500) drops and then a 24×50 mm cover glass (Cancer Diagnostics, Cat. #GC2450-ACS), and allowed to cure for up to 2 nights in the 4 C refrigerator.

Cells were imaged with a 63× lens on a Confocal LSM 510 (Carl Zeiss, Germany) with 405 and 488 nm laser bands.

Intensity quantification. The intensity of Ki-67 expression was quantified using Zen Lite 3.1 from Zeiss. Nuclei were outlined with Spline Contour tool in each image (image size: 108.36 μm×108.36 μm, scale bar 50 μm). The average intensity of Ki-67 staining of each nucleus within the outline was measured by Zen Lite 3.1 and exported to and plot by Microsoft Excel. Five images were analyzed for each condition, and in the cases when there were no cells remaining after the CAP treatment, the cell count was recorded as 0.

RNA-Seq-Library Preparation rRNA depletion and HiSeq Sequencing. MDA-MB-231 cells were CAP treated at 120 p (28.7 W) for 5 mins according to the method mentioned above and incubated for 6 hours. Total RNA were isolated by a guanidinium-phenol (TRIzol)-based kit (Zymo Research Direct-zol) with double Dnase digestion following manufacturer's instructions. RNA samples were quantified using Qubit 2.0 Fluorometer (Life Technologies, Carlsbad, CA, USA) and RNA integrity was checked with 4200 TapeStation (Agilent Technologies, Palo Alto, CA, USA).

rRNA depletion was performed using Ribozero rRNA Removal Kit (Illumina, San Diego, CA, USA). RNA sequencing library preparation used NEBNext Ultra RNA Library Prep Kit for Illumina by following the manufacturer's recommendations (NEB, Ipswich, MA, USA). Briefly, enriched RNAs were fragmented for 15 minutes at 94° C. First strand and second strand cDNA were subsequently synthesized. cDNA fragments were end repaired and adenylated at 3'ends, and universal adapter was ligated to cDNA fragments, followed by index addition and library enrichment with limited cycle PCR. Sequencing libraries were validated using the Agilent Tapestation 4200 (Agilent Technologies, Palo Alto, CA, USA), and quantified by using Qubit 2.0 Fluorometer (Invitrogen, Carlsbad, CA) as well as by quantitative PCR (Applied Biosystems, Carlsbad, CA, USA).

The sequencing libraries were multiplexed and clustered on 1 lane of a flowcell and loaded on the Illumina HiSeq instrument according to manufacturer's instructions. The samples were sequenced using a 2×150 Paired End (PE) configuration. Image analysis and base calling were conducted by the HiSeq Control Software (HCS). Raw sequence data (.bcl files) generated from Illumina HiSeq was converted into FASTQ files and de-multiplexed using Illumina's bcl2fastq 2.17 software. One mismatch was allowed for index sequence identification. rRNA depletion was performed using Ribozero rRNA Removal Kit (Illumina, San Diego, CA, USA). RNA sequencing library preparation used NEBNext Ultra RNA Library Prep Kit for Illumina by following the manufacturer's recommendations (NEB, Ipswich, MA, USA). Briefly, enriched RNAs were fragmented for 15 minutes at 94° C. First strand and second strand cDNA were subsequently synthesized. cDNA fragments were end repaired and adenylated at 3'ends, and universal adapter was ligated to cDNA fragments, followed by index addition and library enrichment with limited cycle PCR. Sequencing libraries were validated using the Agilent Tapestation 4200 (Agilent Technologies, Palo Alto, CA, USA), and quantified by using Qubit 2.0 Fluorometer (Invitrogen, Carlsbad, CA) as well as by quantitative PCR (Applied Biosystems, Carlsbad, CA, USA)."

Data Analysis. After investigating the quality of the raw data, sequence reads were trimmed to remove possible adapter sequences and nucleotides with poor quality using Trimmomatic v.0.36. The trimmed reads were mapped to the *Homo sapiens* reference genome available on ENSEMBL using the STAR aligner v.2.5.2b. The STAR aligner is a splice aligner that detects splice junctions and incorporates them to help align the entire read sequences. BAM files were generated as a result of this step. Unique gene hit counts were calculated by using feature Counts from the Subread package v.1.5.2. Only unique reads that fell within exon regions were counted. After extraction of gene hit counts, the gene hit counts table was used for downstream differential expression analysis. Using DESeq2, a comparison of gene expression between the groups of samples was performed. The Wald test was used to generate p-values and Log 2 fold changes. Genes with adjusted p-values <0.05 and absolute log 2 fold changes >1 were called as differentially expressed genes for each comparison. A gene ontology analysis was performed on the statistically significant set of genes by implementing the software GeneSCF. The goa human GO list was used to cluster the set of genes based on their biological process and determine their statistical significance. A PCA analysis was performed using the "plotPCA" function within the DESeq2 R package. The plot shows the samples in a 2D plane spanned by their first two principal components. The top 500 genes, selected by highest row variance, were used to generate the plot.

Real-Time qPCR Validation

Real-time qPCR (qRT-PCR) was performed to further validate selected differentially expressed Histone RNAs from the NGS results. First strand synthesis was carried out with lug total RNA from CAP treated and mock control MDA-MB-231 cells using random hexamer primers (for mRNA and lncRNA) with a Reverse Transcription SUPERSCRIPT IV 1 ST STRND SYS™ (Thermo, USA) followed by real-time quantitative PCR amplification of the cDNA (50 ng) in an BIO-RAD CFX96 RealTime PCR Detection System (BIO-RAD, USA) using PowerUp™ SYBR™ Green Master Mix (Thermo, USA) and the Each sample was analyzed in triplicate. Internal control housekeeping genes 18s rRNA was selected as described previously (de Kok, J. B. et al. Normalization of gene expression measurements in tumor tissues: comparison of 13 endogenous control genes. Lab Invest 85, 154-159, doi:10.1038/labinvest.3700208 (2005)) and was used for normalized of all samples and subsequently fold changes were calculated using the 2-$\Delta\Delta$CT method (Livak, K. J. & Schmittgen, T. D. Analysis of relative gene expression data using real-time quantitative PCR and the 2(-Delta C(T)) Method. Methods 25, 402-408, doi:10.1006/meth.2001.1262 (2001)). To detect the DNA contamination, diluted RNA samples without first strand synthesis were directly used for qPCR described above. Statistical analysis was performed using the repeated measures ANOVAs followed by post-hoc comparisons using Student t test with Bonferroni corrections as appropriate. $p<0.05$ was considered statistically significant.

8-Oxoguanine (8-oxoG) Modification of RNA

Peptide Synthesis. A (Alexa 488-TaT-S3) peptide was synthesized by solid-phase peptide synthesis at ThermoFisher Scientific USA with the following sequence [NH2]C (Alexa 488) GVLRFIMESGAKGSEVVVSGG-GYGRKKRRQRRR[COOH](SEQ ID NO: 1). The Alexa 488 dye was added to a cysteine at the N-terminal end using maleimide chemistry. The peptide was purified by High-performance Liquid chromatography (HPLC) and fried-dried after cleavage. The peptide (Alexa 488-TaT-S3) is designed for detection of 8-oxoguanine using fluorophore-labelled probe with cell penetrating ability as described previously by Kang, D. M. et al. referring to the detection of 8-oxoguanine and apurinic/apyrimidinic sites using a fluorophore-labelled probe with cell-penetrating ability. BMC Mol Cell Biol 20, 54, doi:10.1186/s12860-019-0236-x (2019)). The amino acids sequence GVLRFIMESGAKGCEVVVSG (SEQ ID NO: 2) is obtained from human ribosomal protein S3 (hRpS3) that tightly binds 8-oxoG sites. In the peptide of the present invention a serine was intentionally substituted for the cysteine in the naturally occurring human ribosomal protein S3 (hRpS3) amino acid sequence. The peptide sequence YGRKKRRQRRR (SEQ ID NO: 3) is from the transactivator (TAT) domain of human immunodeficiency virus-1 (HIV-1) TAT protein that can effectively deliver proteins into cells and appears to not be limited by the size of the fusion protein. "GG" amino acids are the GG linker to bind TAT peptide to S3 peptide.

In situ detection of 8-oxoG RNA. MDA-MB-231 cells were seeded 12 well plates at 105/well and cultured at standard conditions for 24 hrs as described before. Alexa 488-TaT-S3 peptide at 1.0 µM final concentration was added to the cells and incubated for 2 hours. CAP treatment at 120 p (28.7 W) for 5 mins were carried out and the cells were incubated for 24 hrs followed by washing with PBS. Fluorescence signal was read with a BioTek Synergy HTX (Winooski, VT, USA) microplate reader at 485 nm.

Peptide Synthesis. Peptides were synthesized by solid-phase peptide synthesis using Wang resin (Sigma-Aldrich, St. Louis, MO, USA). The peptides were labeled in dimethylformamide (DMF) with five molar equivalents of dye (FPR-552; BioActs, Incheon, South Korea) at the amine of the N-terminal glycine while the resin and protecting group were still intact. After Peptide Synthesis.

Pull-Down

RNA preparation. MDA-MB-231 cells were CAP treated at 120 p (28.7 W) for 5 mins according to the method mentioned above and one set of cells were processed immediately (zero hour), and the other set were incubated for 1 hour. Total RNA were isolated by a guanidinium-phenol (TRIzol)-based kit (Zymo Research Direct-zol) with triple DNase I digestion according to manufacturer instructions (Zymo Research). Ribosomal RNA (rRNA) was depleted using Ribo-Zero Gold rRNA Removal Kit (Illumina, San Diego, CA) following the manufacturer's instructions. Immunoprecipitations of 8-oxoG-containing RNA transcripts were performed as described previously[69] in biological triplicates for CAP treated Zero (CP0) and one hour (CP1), Mock Zero (MZ) and one hour (M1) conditions. Briefly each sample was divided into portions and a portion of the input RNA was incubated with 10 g of 8-oxo-7,8-dihydroguanosine (8-oxoG) monoclonal antibody (Trevigen, Gaithersburg, MD) in immunoprecipitation (IP) buffer (10 mM Tris pH 7.4, 150 mM NaCl, 0.1% IGEPAL, and 200 units/ml SUPERaseIn RNA inhibitor [ThermoFisher Scientific]) in a 1 ml reaction volume for 4 h at 4° C. with rotation. The 8-oxoG antibody binds specifically to 8-oxoG-containing transcripts directly without mediation through an RNA-binding protein. SureBeads Protein A magnetic beads (Bio-rad, Hercules, CA) were washed according to manufacturer's protocol and blocked in IP buffer supplemented with 0.5 mg/ml bovine serum albumin (BSA) for two hours at room temperature. After washing beads twice in IP buffer, the beads were resuspended in IP buffer, mixed with the RNA-antibody reaction and incubated for 2 h at 4° C. with rotation. Next, the beads were washed three more times in IP buffer before two rounds of competitive elution were performed. Each elution consisted of incubation of the beads with 100 g of 8-oxo-dG (Cayman Chemical, Ann Arbor, MI) in IP buffer for 1 h at 4° C. with rotation. The elution volume was then cleaned up using the RNA Clean and Concentrator-5 kit (Zymo Research, Irvine, CA) to isolate Mock Zero ($MZ_{IP}$), one hour ($M1_{IP}$), CAP Zero ($CP0_{IP}$) and one hour ($CP1_{IP}$) RNA. First strand synthesis was performed for the 8-oxoG Immunoprecipitated and input RNA followed by real-time qPCR (qRT-PCR) for Histone RNAs.

Statistics

All assays were repeated at least 3 times and data was plotted by Microsoft Excel 2016 as the mean±standard error of the mean. Data were analysed by ANOVA, post-hoc comparisons were carried out using the Student's t tests with Bonferroni corrections as appropriate. A p value <0.05 was considered statistically significant. The differences were considered statistically significant for *p<0.05, p<0.01, and *p<0.001.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto and their equivalents. The entirety of each of the aforementioned documents is incorporated by reference herein.

SEQUENCE LISTING

```
Sequence total quantity: 4
SEQ ID NO: 1            moltype = AA  length = 34
FEATURE                 Location/Qualifiers
source                  1..34
                        mol_type = protein
                        organism = synthetic construct
SITE                    1
                        note = Cysteine side chain modified with Alexa 488 via a
                          thioether bond
SEQUENCE: 1
CGVLRFIMES GAKGSEVVVS GGGYGRKKRR QRRR                                    34

SEQ ID NO: 2            moltype = AA  length = 20
FEATURE                 Location/Qualifiers
source                  1..20
                        mol_type = protein
                        organism = Homo sapiens
SEQUENCE: 2
GVLRFIMESG AKGCEVVVSG                                                    20

SEQ ID NO: 3            moltype = AA  length = 11
FEATURE                 Location/Qualifiers
source                  1..11
                        mol_type = protein
                        organism = Human immunodeficiency virus 1
SEQUENCE: 3
YGRKKRRQRR R                                                             11
```

```
SEQ ID NO: 4            moltype = AA  length = 4
FEATURE                 Location/Qualifiers
source                  1..4
                        mol_type = protein
                        organism = unidentified
SEQUENCE: 4
DEVD                                                                    4
```

What is claimed is:

1. A method for monitoring levels of oxidized histone mRNA in breast cancer cells, comprising the steps of:
   treating breast cancer cells with cold atmospheric plasma (CAP);
   isolating histone mRNA from the CAP-treated breast cancer cells;
   incubating the histone mRNA with a peptide according to SEQ ID NO: 1; and
   determining the levels of oxidized histone mRNA by measuring a fluorescence intensity.

2. The method according to claim 1 wherein the fluorescence intensity is determined by microscopy or microplate reader with appropriate settings.

3. The method according to claim 1 wherein the histone mRNA is 8-oxoguanine modified.

4. The method according to claim 1 wherein the CAP treatment employs cold plasma at less than 35° C.

5. The method according to claim 1 wherein the method is performed 6, 12, 24 or 48 hours post CAP treatment.

6. The method according to claim 1 wherein the method comprises the step of a differential expression analysis between groups of samples for the isolated histone mRNAs.

7. The method according to claim 6, wherein the isolated histone mRNA levels of histones selected from the group consisting of HIST1H1C; HIST1H2AB; HIST1H2AC; HIST1H2AG; HIST1H2AI; HIST1H2BJ; HIST1H2BK; HIST1H2BN; HIST1H2BO; HIST1H3A; HIST1H3B; HIST1H3C; HIST1H3H; HIST1H4B; HIST2H3D and HIST4H4 are determined.

8. A peptide (Alexa 488-TaT-S3) synthesized by solid-phase synthesis with the following sequence [NH2]C (Alexa 488) peptide GVLRFIMESGAKGSEVVVSGG-GYGRKKRRQRRR[COOH] (SEQ ID NO: 1).

* * * * *